(12) United States Patent
Tamari

(10) Patent No.: US 6,773,425 B1
(45) Date of Patent: Aug. 10, 2004

(54) CONTAINER FOR BIOLOGICAL PRODUCTS REQUIRING CELLULAR STASIS

(76) Inventor: Yehuda Tamari, 21 Singworth St., Oyster Bay, NY (US) 11771-3703

( * ) Notice: Subject to any disclaimer, the term of this patent is extended or adjusted under 35 U.S.C. 154(b) by 0 days.

(21) Appl. No.: 10/364,816

(22) Filed: Feb. 11, 2003

Related U.S. Application Data

(63) Continuation-in-part of application No. 10/038,688, filed on Jan. 2, 2002, now Pat. No. 6,517,526, which is a continuation-in-part of application No. 09/754,045, filed on Dec. 29, 2000, now abandoned.

(51) Int. Cl.[7] .............................................. B65D 81/18
(52) U.S. Cl. ......................... 604/403; 383/38; 604/408; 604/410
(58) Field of Search ................................ 604/403, 408, 604/410; 383/38

(56) References Cited

U.S. PATENT DOCUMENTS

| | | | | |
|---|---|---|---|---|
| 4,609,102 A | * | 9/1986 | Blum | 206/216 |
| 4,973,327 A | * | 11/1990 | Goodrich et al. | 604/408 |
| 5,257,983 A | * | 11/1993 | Garyantes et al. | 604/403 |
| 5,309,649 A | * | 5/1994 | Bergmann et al. | 34/284 |
| D425,205 S | * | 5/2000 | Henigan et al. | D24/216 |
| D430,939 S | * | 9/2000 | Zukor et al. | D24/216 |
| 6,517,526 B1 | * | 2/2003 | Tamari | 604/403 |

* cited by examiner

Primary Examiner—Gerald A. Michalsky

(57) ABSTRACT

The invention is an improved container for collecting, freeze-drying, storing, reconstituting, and administering biological solutions and, in particular, blood products. The container features a pliable bottom wall providing intimate thermal contact with the cooling/heating shelf of the lyophilizer; a top wall incorporating a hydrophobic membrane providing a path for water vapor and a bacterial barrier; and side walls sufficiently stiff to support the ceiling but preferably also sufficiently flexible to collapse and minimize storage space especially once lyophilization is complete. The walls incorporate sealable ports that can be used to load the solution for processing and/or adding reconstituting liquids and/or administering the reconstituted solution to a patient. The top wall may incorporate a removable cover that protects the membrane before freeze-drying takes place. A secondary pouch encloses the container immediately post-lyophilization and may incorporate means to evacuate its inner space thereby reducing space and limiting the gas volume the final product is exposed to during storage.

68 Claims, 10 Drawing Sheets

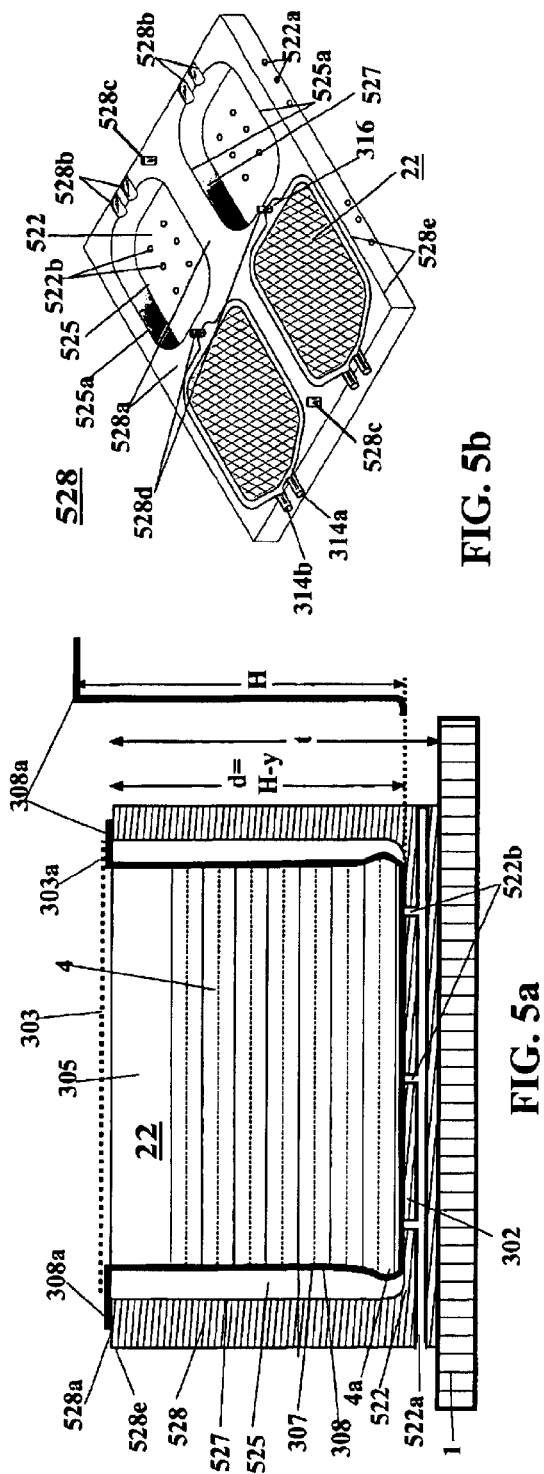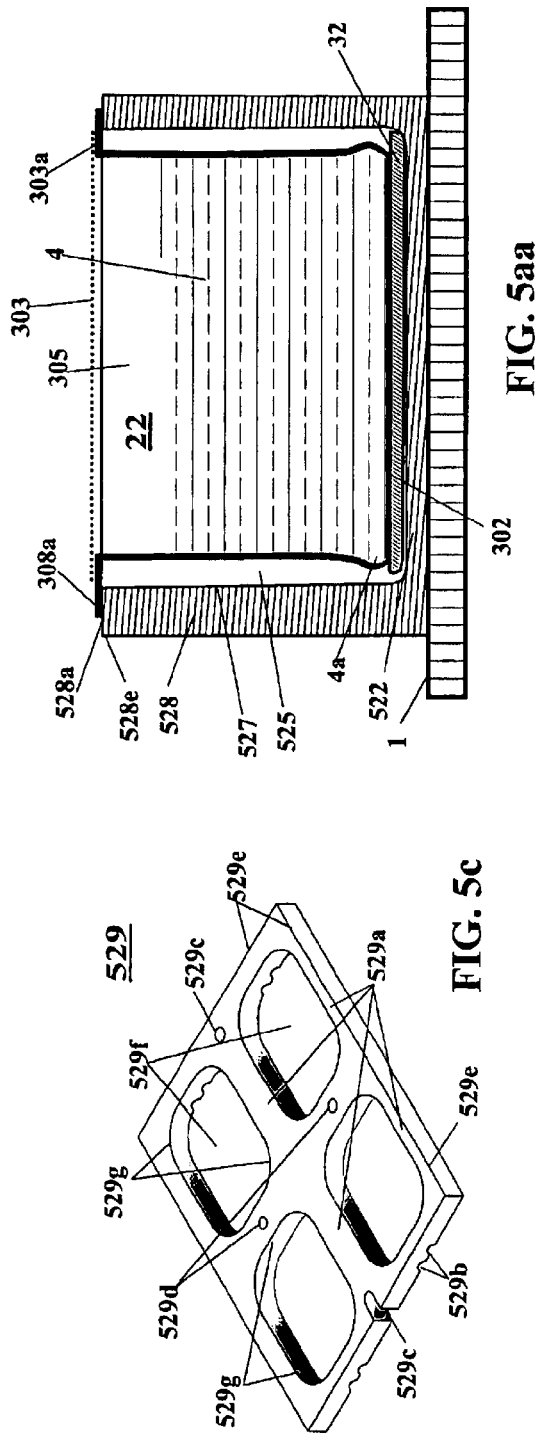

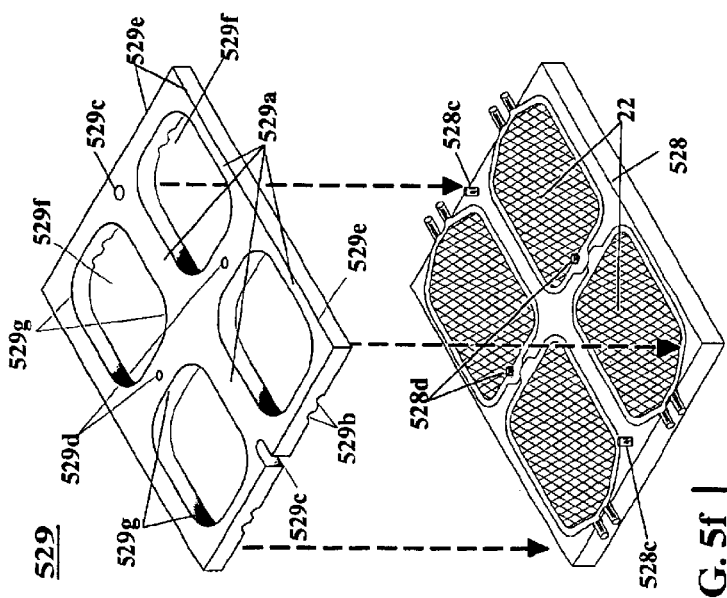
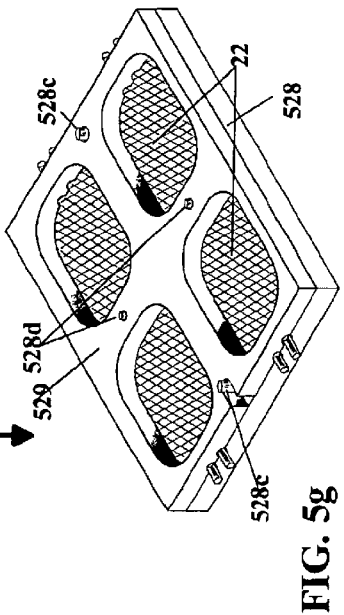
FIG. 5f
FIG. 5g
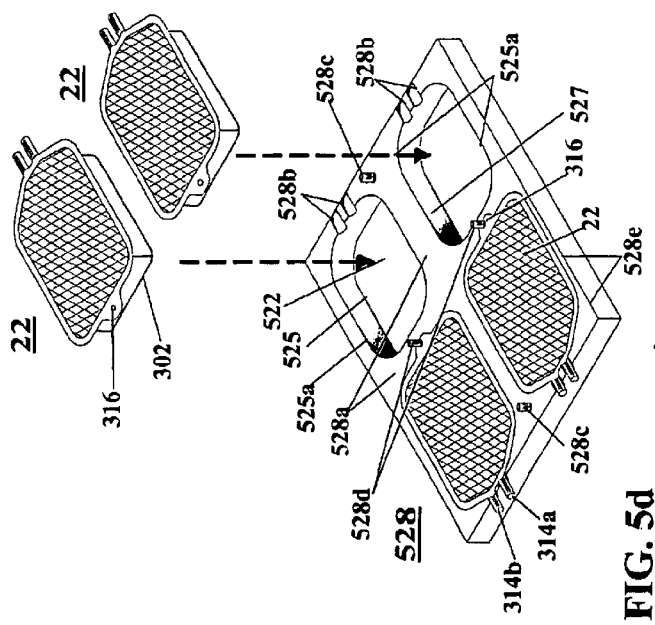
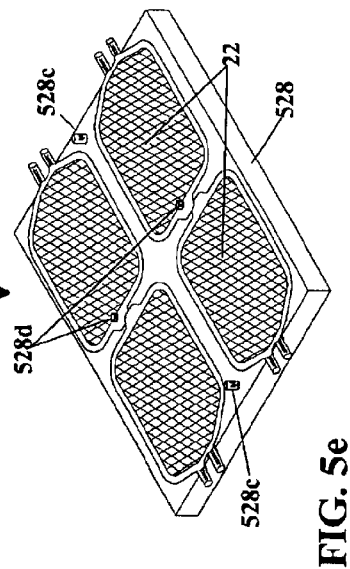
FIG. 5d
FIG. 5e

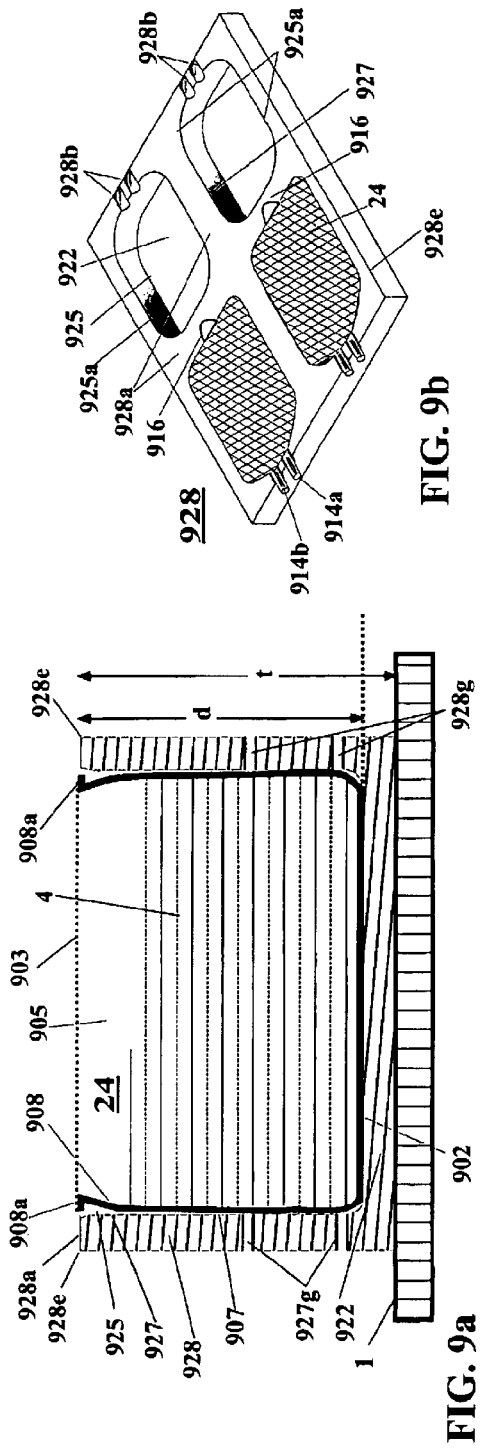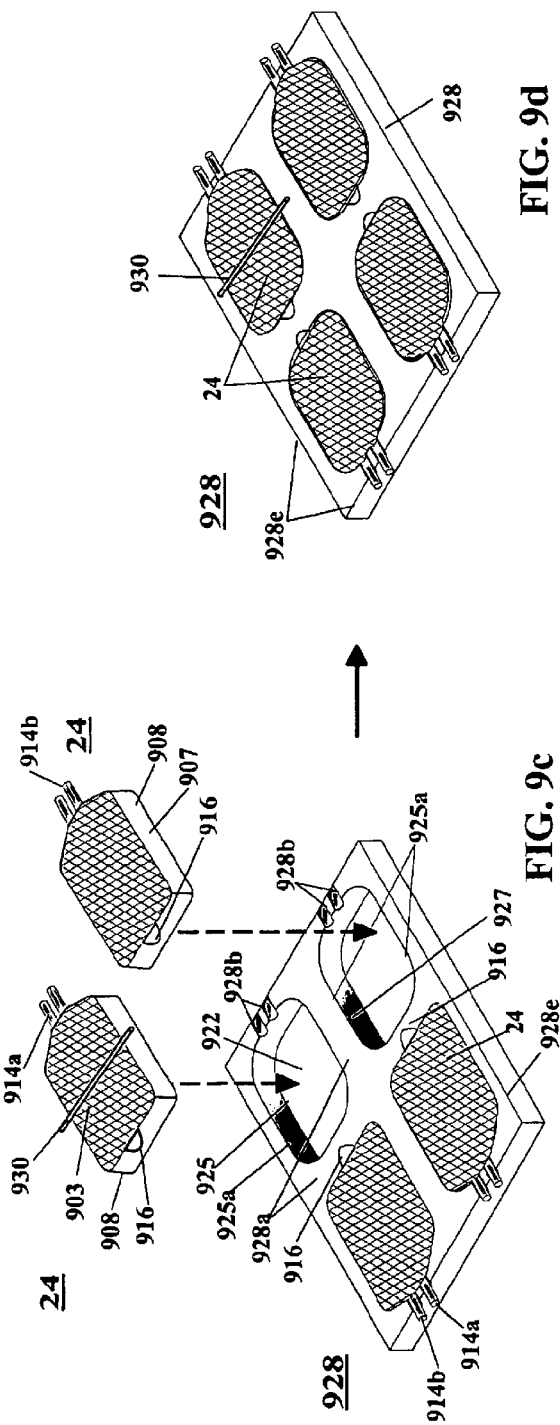

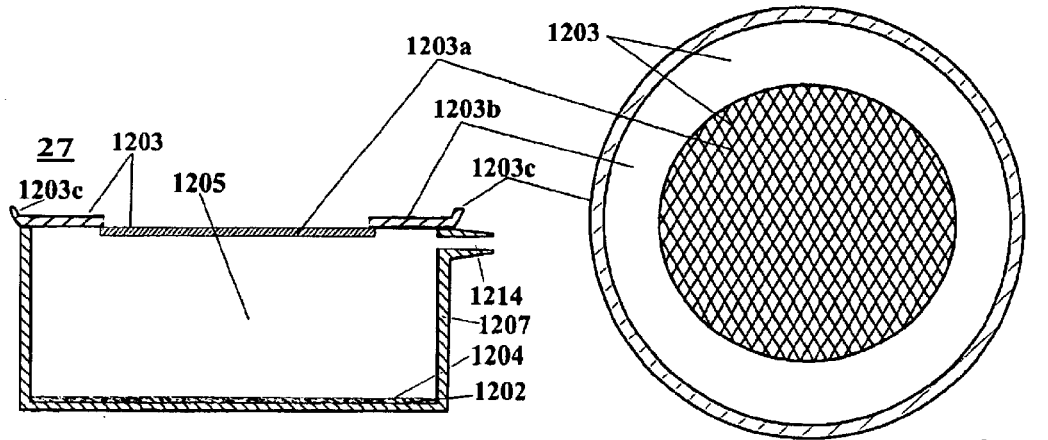
FIG. 12a  FIG. 12b
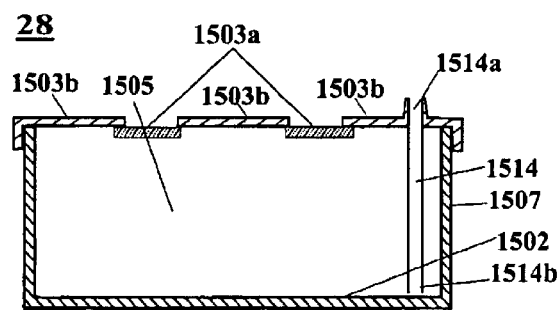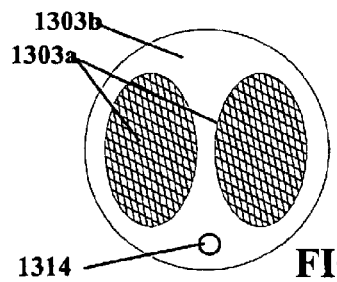
FIG. 15  FIG. 13
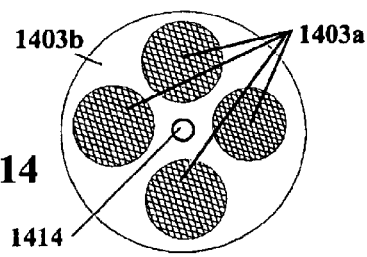
FIG. 14
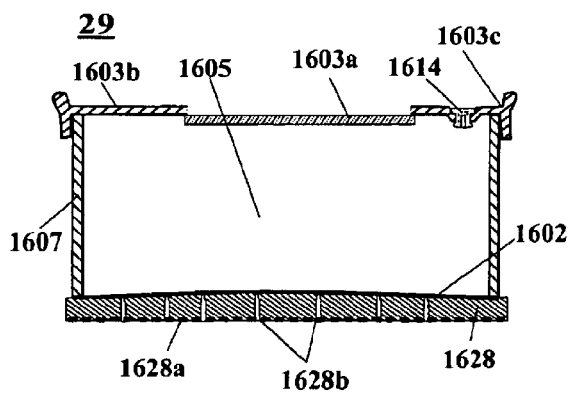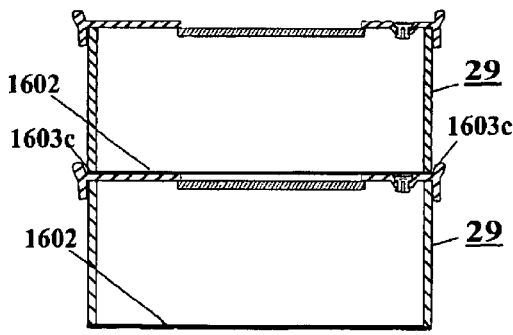
FIG. 16a  FIG. 16b

CONTAINER FOR BIOLOGICAL PRODUCTS REQUIRING CELLULAR STASIS

CROSS-REFERENCE TO RELATED APPLICATIONS

This application is a continuation in part of application U.S. Ser. No. 10/038,688, filed Jan. 2, 2002, now U.S. Pat. No. 6,517,526 issued Feb. 11, 2003, which is a continuation-in-part of U.S. Ser. No. 09/754,045, filed Dec. 29, 2000, now abandoned, the disclosure of said applications and issued patent being incorporated herein by reference thereto.

GOVERNMENT INTERESTS

This invention was in part made with government support under SBIR Grants N00014-97-C-0016 and N00014-99-C-0290 awarded by the Office of Naval Research and Defense Advanced Research Projects Agency (DARPA) Contract N6001-02-C-8071. As such the government may have certain rights in the invention.

BACKGROUND OF THE INVENTION

1. Field of the Invention

The present invention in its simplest form is a container for freeze-drying and storing pharmaceutical material. In its more expanded form it serves to collect, process, freeze-dry, store, reconstitute and utilize biological and/or pharmaceutical material solutions preferably under sterile conditions. In one preferred form the container can be collapsed to accommodate the volume of the freeze-dried product during storage and expanded to the volume corresponding to the rehydrated product. Hereinafter, the use is made of blood products, and the special needs associated with such product, as the lyophilized product is for description purposes and by no means should be taken as a limitation of the invention.

2. Description of the Related Art

Lyophilization is used to increase the shelf life of biological/pharmaceutical solutions by freezing the solution and then removing the solvent (usually water) by applying high vacuum. The rate of lyophilization is dependent on the vapor pressure of the drying mass, which in turns depends on the heat transferred by conduction from the shelf of the lyophilizer to the top of the frozen mass where evaporation occurs. The dehydrated frozen mass, or cake, is then stored until it is reconstituted by adding a solvent similar to that removed and then used as intended.

U.S. Pat. No. 4,973,327 of Goodrich et. al. of Cryopharm Corp discloses many of the desirable features of the present invention as described in the Abstract: "A lyophilization bag is provided in which a fluid, such as blood, may be introduced, lyophilized without collapsing the bag, stored, reconstituted and distributed from the bag without intermediate transfer of the useful contents from the bag".

U.S. Pat. No. 5,257,983 discloses a container with its flexible peripheral walls reinforced with rigid structures to prevent its inward collapse and a bottom wall made of a rigid material. Samples of the last containers made by Cryopharm (obtained from Dr. Goodrich) were square rigid trays 1" high 10"×10" made of polyester film 0.020" thick.

Bergmann's U.S. Pat. No. 5,309,649 discloses "a container for freeze drying materials under sterile conditions, wherein the sides of the container consist at least partly of a hydrophobic, porous, germ-impermeable, water vapor-permeable membrane." Two forms of the container were described: a bag and a rigid rectangular tray both covered with the membrane. In 1995 W. L. Gore introduced the Lyoguard bag, a single-use sterilizable processing bag providing a protective barrier before, during and after freeze drying (Flyer #LP001:03/08/95 and a brochure from W.L. Gore & Associates, Inc. Microfiltration Technologies Group, Elkton Md.) that looks very much like that shown by FIG. 2 of '649. The bag described by Pat. '649 and Gore's bag are open along one entire side to allow product introduction after which the open side of the bag is heat-sealed. Further, both are made with two layers, a floor and a roof, with the roof incorporating a hydrophobic membrane. Neither have sidewalls. Pat. '649 also illustrates a tray covered with a hydrophobic membrane, described as a " . . . trough (tray) consists of liquid-impermeable synthetic resin and preferably has a wall thickness of 0.5 to 1 mm" (i.e. 0.020 to 0.040" thick).

U.S. Des. Pat. Nos. D430,939 and D425,205 and resulting Lyoguard tray (W.L. Gore & Associates) illustrate a rigid wall container topped with a hydrophobic membrane with a flexible, transparent, thin-film bottom that closely conforms to the lyophilizer shelf for more efficient heat transfer. It also incorporates a large top port positioned above the floor of the tray.

Each of the prior art containers suggests useful features yet all can be improved. There are no prior art containers that provide a simple collapsible container having a flat bottom that conforms to the shelf of the lyophilizer or that provides the rectangular shape so useful for lyophilization. Some collapsible tray-shaped containers are complicated and require additional steps to receive and remove reinforcing members that allow the container to collapse or maintain its shape during lyophilization. Other trays used for lyophilization have a relatively heavy wall that results in at least two factors that reduce heat transfer between the shelf and the product. First, the thicker the floor of the tray, the greater the resistance to heat transfer. Second, and more importantly, it is almost impossible to maintain the bottom of a rigid thin plastic tray completely flat against the shelf of the lyophilizer. Though the product to be lyophilized weighs down the bottom of the tray downward towards the shelf, the weight of its thin layer (usually less than 10 mm) is insufficient. Thus, a bottom made of a noncompliant material will result in a non-conforming floor with some sections lifting off the shelf preventing said sections from having intimate shelf contact causing inefficient and non-uniform heat transfer. The latter, may result in non-uniform lyophilization of the product, which can lead to a final, less viable end product. Certainly, poor heat transfer would slow down the freezing and the warming of the product required for the process thereby increasing cost. A tray with a rigid wall also prevents reduction of the tray's volume prior to and/or after lyophilization. Since the product's volume relative to that of the tray is small before lyophilization and even smaller after lyophilization, it leads to unnecessary storage expenses especially when the lyophilized product has to be stored in a freezer.

Prior art bags designed for lyophilization, utilizing a hydrophobic membrane as the top wall, were made without side walls and without ports. Thus, when filled with a solution and placed on a lyophilizer shelf, the bag would have a cross-section that is tear-shaped, see FIG. 1a. This shape of the prior art bags presents two drawbacks for lyophilization. First, the contacting surface of the bottom of the bag with the shelf is limited to the midsection, while the sides are raised above the shelf, see FIG. 1a. As a consequence, less than 50% of the bottom surface may be available for direct heat transfer between the shelf and the product during both the freezing cycle and lyophilization (heating) cycle. The tear shaped cross-section also results in a non-uniform thickness of the product being lyophilized, which may cause product damage due to non-uniform freezing. Also, inefficient use of the lyophilizer is evident from the thinner sections drying much faster than the thicker midsection, and the tear-shaped tray results in lower product volume per foot print. Secondly, flexible containers without sidewalls are more likely to have the product contacting the membrane, resulting in, the product freezing against the membrane; the product would then dry against and plug up the membrane. Plugging of the membrane would result in reduction of the lyophilization rate. Furthermore, the lack of ports limits the usefulness of such bags, or requires complicated and expensive procedures to maintain sterility prior to lyophilization and when the product is to be used. The prior art also requires a heat sealer to seal the container once filled with product.

In general, molecules leaving any point along the top of a frozen mass can be viewed as a solid angle or a cone with its peak being the point on the surface of the product and its base, the perimeter of the membrane. The rate of evaporation depends on that solid angle. If part of the roof is blocked, the degree of blockage is dependent on the solid angle defined by the point on the surface and the external perimeter of the block. It is also possible to raise the membranous roof "far" above the product thereby decreasing the solid angle of blockage and increasing the chance of molecules "seeing" the hole. However, raising the roof above the product decreases the ratio of product volume to lyophilizer container volume, wasting valuable lyophilizer space and storage space. Therefore, lyophilization rate can be improved by assuring that the footprint of the membrane corresponds as close as possible to the footprint of the floor. Improvement in the prior art design, such as reducing or eliminating non-membrane area over the product to be lyophilized, would be welcomed.

The rapid treatment of injured or diseased troops may be facilitated with the use of adult mesenchymal stem cells (MSCs) to initiate rapidly the regeneration of many connective tissues, e.g., muscle, bone, cartilage, tendon, ligaments, etc. Currently, storage and delivery of these cells requires temperatures lower than −120° C., which is impractical or impossible in the military environment. Similarly, biomatrices seeded with cultured chondrocytes enhance the quality of the articular cartilage repair tissue in traumatic knee injuries. Each of these applications requires the technology to process, store and reconstitute the final product even under battlefield conditions.

Many biological assays require standards, or controls for validation. Some standards come in ampoules and many have to be refrigerated or frozen. A packaging system that allows biological standards to be stabilized by desiccation or lyophilization to improve their shelf-life and/or reduce the need for cold storage would be welcomed. Such a package, formed into multicavity entity, with each cavity individually filled by identical product of specific dosage. Having a package where each cavity can be opened without affecting the product in the other cavities (similar to multi lozenge dispenser) would also be welcomed.

BRIEF SUMMARY OF THE INVENTION

It is therefore the objective of the present invention to provide a lyophilization container for collecting, processing, freeze drying, storing, reconstituting and utilizing biological and/or pharmaceutical products preferably maintaining sterile conditions.

It is a primary object of the invention to provide a lyophilization container comprising of a compliant bottom, foldable sidewalls, and a hydrophobic membrane as a top wall. The container preferably is designed for blood products but is adoptable to other products that would benefit from the design features of the invention such as having a flat pliable bottom that conforms to the shape of the lyophilizer's shelf that it is placed on, allowing heat transfer essentially across its entire bottom, providing a uniform thickness of product to be lyophilized that assures more uniform, safer, faster, and more efficient lyophilization process, as well as, achieving a greater product volume capacity for the same shelf area.

It is also the objective of the present invention to provide a lyophilization container with a hydrophobic membrane as a "roof" that provides a fluid path for vapor but not for liquids while acting as a barrier to bacteria.

In addition, the present invention provides a lyophilization container with removable means to cover the hydrophobic "roof", said cover rendering said membrane inoperative until said means are removed, thereby protecting the membrane during any processing required before the lyophilization process.

Another objective of the present invention is to provide a lyophilization container with means to support the hydrophobic "roof" from contacting the product during the lyophilization process.

Yet another objective of the present invention is to provide a lyophilization container with side ports that allow the user to introduce the rehydration solution and/or administer the rehydrated solution to the patient in a sterile manner.

It is also the objective of the present invention to provide a lyophilization container having a low profile and a high ratio of product volume to container volume as well as allow loading the product with minimal reduction in the membrane area available for lyophilization.

It is also the objective of the present invention to provide a lyophilization container that can be used as a rigid container but can also be collapsed prior to and post lyophilization thereby reducing storage costs. Further, the container may be expanded to the volume corresponding to the rehydrated product.

It is another objective of this invention to provide devices that would enhance the production, storage, shipping, and reconstitution of products (e.g. RBC, MSC) requiring long-term stabilization by lyophilization or desiccation. These include culture dishes as well as single or multiwell flasks modified to enhance heat transfer, maintain sterility, and allow controlled rehydration of the product by the end user. Modification may include a thinner floor, a more conductive floor, designs that provide intimate contact and a thermally conductive plate that provides more uniform temperature across the floor of the containers.

The force exerted by the weight of products with low volume but large surface area (e.g. cells adhering to the floor of a culture dish) may be insufficient to displace a compliant floor to form intimate contact with the shelf of a lyophilizer. It is therefore another objective of the present invention to provide culture dishes (e.g. Falcon #353801) or multiwell flasks (e.g. Falcon #353224) modified to enhance heat transfer between their floor and the shelf of the lyophilizer. These containers also incorporate hydrophobic membranes to allow water vapor transfer while maintaining sterility of the product.

It is another objective of the present invention to provide a multicavity container for drying by lyophilization or desiccation, with each cavity individually filled with an identical product of a specific dosage, and where each cavity can be separated from the other cavities and processed (i.e. rehydrated) without affecting the product in the other cavities (similar to multi lozenge dispenser).

Other innovative and useful features of the present invention will become apparent in the specification given below. It should be emphasized that the use of blood products as the lyophilized product in describing the invention is for descriptive purposes only and should not be taken as a limitation of the invention in any shape or form.

BRIEF DESCRIPTION OF THE DRAWINGS

FIG. 3b is a cross sectional representation of a side view of the lyophilization bag shown in FIG. 3a.

FIG. 3ba is a cross sectional representation of a side view of the lyophilization bag shown in FIG. 3b with its membrane concave relative to the floor to prevent contact with the product.

FIG. 3bb is a cross sectional representation of a side view of the lyophilization bag shown in FIG. 3b post lyophilization with its membrane convex relative to the floor to hold water for controlled rehydration of the product.

FIG. 3cc is a cross sectional view of one preferred embodiment of the lyophilization bag incorporating a smaller hydrophobic membrane that eliminates stagnation areas between the membrane and the landing.

FIG. 4b is a cross sectional representation of a side view of the lyophilization bag shown in FIG. 4a.

FIG. 5a is a cross sectional view of one preferred embodiment of the lyophilization bag combined with a rigid supporting tray.

FIG. 5b is a three dimensional view of one preferred embodiment of two lyophilization bags combined with a multicavity rigid supporting tray.

FIG. 5c is a three dimensional view of one preferred embodiment of a matching flange used in combination with multicavity rigid supporting tray shown in FIG. 5b.

FIG. 5aa is a cross sectional view of one preferred embodiment of the lyophilization bag with a thermal plate between it and the supporting tray.

FIG. 5d is a three dimensional view illustrating how the user would place lyophilization containers in the supporting tray shown in FIG. 5b.

FIG. 5e is a three dimensional view illustrating the supporting tray shown in FIG. 5b filled with four lyophilization containers.

FIG. 5f is a three dimensional view illustrating the alignment and placement of the matching flange to the top of the filled supporting tray shown in FIG. 5e.

FIG. 5g is a three dimensional view illustrating the filled supporting tray shown in FIG. 5e topped with the matching flange shown in FIG. 5c ready to be placed in a lyophilizer.

FIG. 8b is a three dimensional view of the floorless disposable rigid supporting tray shown in FIG. 8a.

FIG. 9a is a cross sectional view of another preferred embodiment of the lyophilization bag combined with a rigid supporting tray.

FIG. 9b is a three dimensional view of another preferred embodiment of two lyophilization bags combined with a multicavity rigid supporting tray similar to that shown in FIG. 5b.

FIG. 9c is a three dimensional view illustrating how the user would place lyophilization containers in the supporting tray shown in FIG. 9b.

FIG. 9d is a three dimensional view illustrating a supporting tray shown in FIG. 9c filled with four lyophilization containers.

FIG. 10b is a top view of the container illustrated in FIG. 10a

FIG. 10c is a top view of the roof used to seal the container shown in FIG. 10a.

FIG. 10e is a side view of a tray used to support the container shown in FIG. 10a.

FIG. 10f is a side view of the container shown in FIG. 10a fitted over the supporting tray shown in FIG. 10e and with the cavities isolated into individual pockets by the membrane shown in FIG. 10c sealed to the weirs of the container shown in FIG. 10a.

FIG. 11b is a bottom view taken along 11b and 11b' of the thermal plate shown in FIG. 11a.

FIG. 12a is a side view of one form of the Lyo-Dish, a modified circular culture dish that allows lyophilization and storage of the biological product requiring metabolic stasis.

FIG. 12b is a top view of the Lyo-Dish shown in FIG. 12a with one hydrophobic membrane incorporated into its roof.

FIG. 13 is a top view of the Lyo-Dish shown in FIG. 12a with two hydrophobic membranes incorporated into its roof.

FIG. 14 is a top view of the Lyo-Dish shown in FIG. 12a with four hydrophobic membranes incorporated into its roof.

FIG. 15 is a side view of another form of the Lyo-Dish, a modified circular culture dish that allows lyophilization and storage of the biological product requiring metabolic stasis.

FIG. 16a is a side view of yet another form of the Lyo-Dish, a modified circular culture dish that allows lyophilization and storage of the biological product requiring metabolic stasis.

FIG. 16b is a side view of illustrating two Lyo-Dishes shown in FIG. 16a stacked atop each other.

DETAILED DESCRIPTION OF THE INVENTION

Figure 1A:
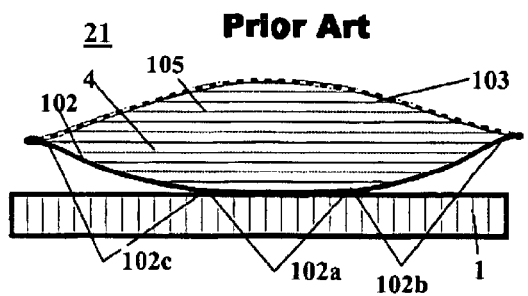
FIG. 1a is a cross sectional view of a typical lyophilization bag incorporating a hydrophobic membrane used in prior art devices filled with a product to be lyophilized.

Reference should now be made to the drawings wherein the last two reference numerals are used throughout to designate the same or similar parts (e.g. membrane 103 and 203 in FIGS. 1 and 2 respectively). It should be noted that the use of blood products is for descriptive purposes, and should not be taken as a limitation to the use of the devices described hereinafter. Below, unless otherwise specified, the term roof and membrane are used interchangeably, both signifying a hydrophobic membrane serving as a roof for the described container. Further, unless otherwise specified, the membrane is hydrophobic that provides fluid communication with the product chamber for vapor but not for liquids or bacteria, and the term sidewall and vertical wall forming the product chamber are used interchangeably. And lastly, all references to specific physical characteristics may be limited by acceptable manufacturing tolerances.

FIG. 1a is a cross sectional view of prior art lyophilization bag 21 incorporating a hydrophobic membrane as its roof. This bag lacks sidewalls. It is formed by sealing floor 102 to roof 103 that incorporates a hydrophobic membrane to form product chamber 105. When filled, chamber 105 forms a pointed ellipsoid cross-section that reduces the contact area, between its floor 102 and lyophilizer shelf 1, to mid-section 102a. Side sections 102c and 102b of floor 102 rise above and therefore do not make thermal contact with shelf 1. The limited contact between floor 102 and shelf 1 limits the heat exchanged between the two surfaces thereby extending the time required to process product 4.

Figure 2A:
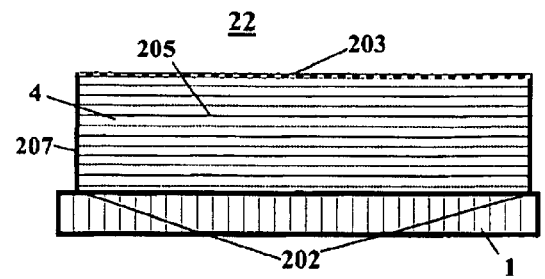
FIG. 2a is a cross sectional view of a lyophilization bag incorporating a hydrophobic membrane of the present invention filled with a product to be lyophilized.
Figure 1B:
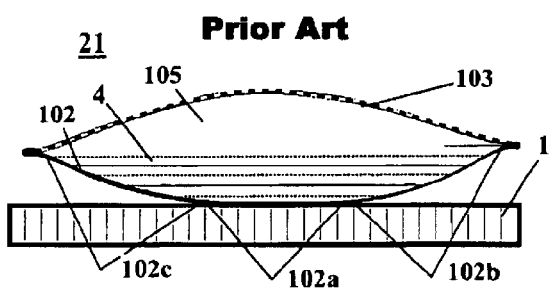
FIG. 1b is a cross sectional view of a typical lyophilization bag incorporating a hydrophobic membrane used in prior art devices filled to a level that prevents the product to be lyophilized from contacting the membrane.
Figure 2B:
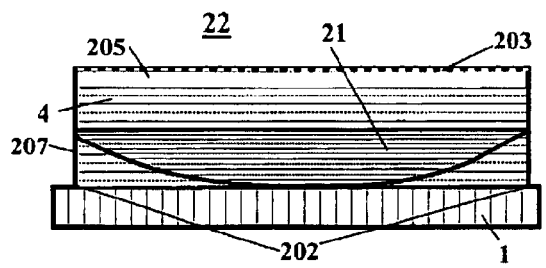
FIG. 2b is a cross sectional view of a lyophilization bag incorporating a hydrophobic membrane of the present invention devices filled to a level that prevents the product to be lyophilized from contacting the membrane.

FIG. 2a is a cross sectional view of lyophilization bag 22 incorporating a hydrophobic membrane according to one form of the present invention. Bag 22 has vertical walls 207, extending from floor 202 and sealed to roof 203, said roof incorporating a hydrophobic membrane to form product chamber 205. When comparing the ellipsoid cross-section of bag 21 to the rectangular cross-section of bag 22, it is clear that filled bag 21, accommodates a lower volume of product 4 than filled bag 22. In addition, it is also important to prevent membrane 103 from contacting product 4 to reduce the possibility of product 4 plugging the pores of said membrane. Under such a preferred filling condition, the relative volume of product 4 that bag 21 can accommodate, shown in FIG. 1b, is even lower than can be accommodated by bag 22, shown in FIG. 2b. This difference is illustrated by superimposing the volume of product 4 in bag 21 as a solid line (labeled 21) over the volume of product 4 in FIG. 2b. In addition to lower filling volume, the non-uniform cross-section, inherent to Bag 21, may result in non-uniform freezing and a lower grade of reconstituted product 4.

Figure 3A:
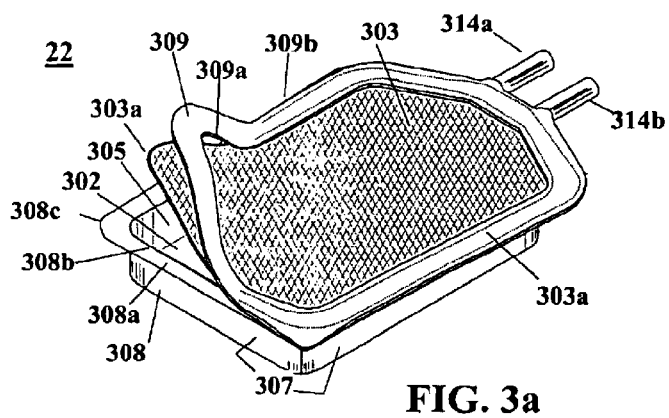
FIG. 3a is a three dimensional view of one preferred embodiment of the lyophilization bag incorporating a hydrophobic membrane according to present invention.
Figure 3B:
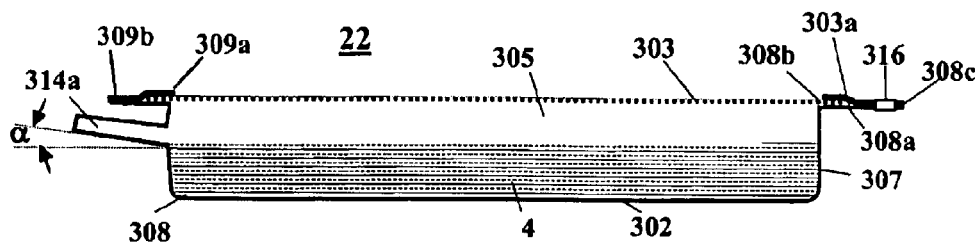
Figure 3B:
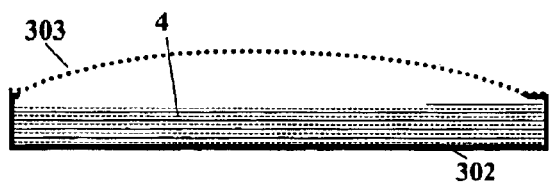
Figure 3B:
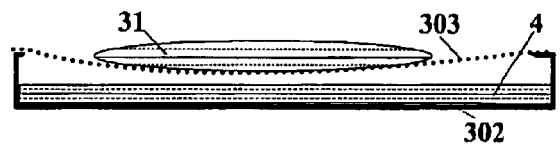

FIG. 3a is a three dimensional illustration of one preferred design of the present invention, an empty Lyo-Bag™, 22, and FIG. 3b is a cross sectional representation of filled bag 22. As with other drawings, the relative dimensions may not be to scale but were chosen to better illustrate the invention; appropriate dimensions are given in the specifications. Here, bag 22 consists of tray 308 having naturally flat rectangular shaped floor 302, said floor extending, along its outside periphery, to form vertical wall 307, said wall ending with landing 308a topped with a hydrophobic membrane serving as roof 303. Note, hereinafter, unless otherwise indicated, the terms "floor" and "roof" refer to opposing planar walls of the lyophilization container when it is placed on a shelf with the membrane being on top. The membrane is sealed along landing 308a to form product chamber 305. Landing 308a is preferably flat, parallel to floor 302, and extending outward from inside periphery 308b to outside periphery 308c. Tray 308 preferably is made of a film that resists tearing (high tear strength), is flexible, can be vacuum formed and heat-sealed, (or ultrasonically welded or RF welded), and at least its inside surface is compatible with product 4 (e.g. polyurethane, polypropylene, polyester). Floor 302 of product chamber 305 should be sufficiently thin and pliable to assure that it conforms to the surface, which it is placed on (i.e. lyophilizer shelf 1) when chamber 305 is filled with product 4. Conformability of floor 302 to shelf 1 (as shown in FIG. 2a by floor 202) assures the intimate contact between the two surfaces necessary for the most efficient thermal transfer between shelf 1 and product 4 via floor 302. Intimate thermal contact is also essential for uniform freezing, and drying, as well as the efficacy of the final product. Floor 302, having a product side and a shelf side, is naturally flat, and is sufficiently conformable to allow the weight of product 4 to smooth out bends in floor 302 that tend to lift floor 302 off shelf 1 due to warping. The minimum force per surface area (pressure, P) required to push floor 302 down against shelf 1 can be expressed as a function of the thickness (e.g. the height or H) of the solution to be processed (product 4) and its density (ρ) in chamber 305 as: $P(gr/cm^2)=\rho(gr/cm^3)*H(cm)$. For example, when lyophilizing blood products, it is standard practice that the thickness (or height) of product 4 in chamber 305 is between 4 and 7 mm. Assuming a minimum height of 4 mm and a solution with a density approximating that of water (1 gr/ml), the pressure required to conform floor 302 to shelf 1 should be less than or equal to 0.4 $gr/cm^2$. Less compliant floor can be used if greater thickness of product 4 is acceptable. For example, for a product thickness of 10 mm, the minimum pressure required to conform floor 302 to shelf 1 should be equal to or less than 1.0 $gr/cm^2$. Representative material and construction are hereinafter described.

Another innovative feature of bag 22 is that its sidewalls 307 are preferably sufficiently stiff to support roof 303 above product 4 yet sufficiently bendable to collapse, much like an IV bag, when reconstituted product 4 is administered to the patient. For example, when roof 303 is made of a membrane that weighs 0.0075 $gr/cm^2$, the wall's stiffness must support a minimum pressure of 0.0075 $gr/cm^2$, or a weight of $0.0075(gr/cm^2)*A_r(cm^2)$, where $A_r$ is the area of the roof. Similarly, a minimum pressure of 10 cm $H_2O$ (the expected minimum height of the an IV bag height above a patient) in product chamber 305, or a force of 10 $gr/cm^2$ should overcome the stiffness of walls 307 and or floor 302, allowing said walls to bend thereby reducing the volume of chamber 305 as the product is administered. Should bag 22 need not collapse during administration of reconstituted product 4, (e.g. air is allowed to enter chamber 305 during administration), yet still collapse for storage, the stiffness of walls 307 may be increased for it to withstand a higher pressure difference across wall 307, a design described in reference to FIG. 6a. It should be clear that the shorter wall 307 is, the less likely it would "buckle" under the weight of the roof, yet it must be high enough to keep roof 303 above product 4. The deleterious effects that result from the product contacting the membrane have been described in reference to the prior art devices. For example, to assure that the membrane does not contact the product, a bag having a 12 cm by 20 cm floor 302 can be utilized for a product that can have a thickness of 8 mm for the lyophilization process, if its wall 307 is at least 10 mm high and preferably 15 mm high. It should be clear that when contact of product 4 with membrane 303 is not detrimental to the lyophilization rate, then wall 307 can be lowered to even allow membrane 303 to contact product 4.

Assuring that membrane 303 does not contact product 4 also requires that any sagging of roof 303 must be less than the difference in height between landing 308a and the top most part of product 4. This can be achieved by having roof 303 sufficiently stiff to support itself from over sagging; a stiffness that depends on the weight of the roof and its unsupported extension over floor 302. An example is Emflon 0.2μ PTFE membrane made by Pall Corp of East Hills N.Y. laminated on one side by Typar® Spunbond polypropylene, weighing 2 oz/yd² (Snow Filtration West Chester Ohio), placed over tray 308 with an inside rectangular periphery 308b of landing 308a nominally being 5"×7". Other designs that limit membrane contact with the product (e.g. membrane 303 shaped concavely relative to floor 302 raises the roof 303 above product 4 as well as stiffens the roof) are possible. Alternatively, the membrane can be held tight along its periphery by stiffer frame 309, as described in more details below, or supported by supporting tray 528 described in reference to FIGS. 5a and 5b.

Bag 22 can, for example, be made by vacuum forming tray 308 using Cryovac multilayer sterilizable medical film (Medical film M321, Duncan, S.C.), which provides heat resistance, gloss and strength (polyester), flexibility and moisture barrier (polyethylene), and biocompatible and sealable surface (polypropylene). The film typically is 0.0075" thick and weighs 17.5 $mg/cm^2$. Thus, a typical Lyo-Bag designed to process 100 ml of product 4 with a 5 mm thickness would have a 200 $cm^2$ floor that weighs 3.5 gr. Roof 303, frame 309 and landing 308a can be sealed to form bag 22 using, for example, heat-sealing, ultrasonic sealing, or adhesives/sealants or a combination of such processes that are suited for the materials used and the manufacturing tools available. It should be clear that all components used to form bag 22 preferably withstand temperatures of at least as low as −60° C. (lyophilizer temperature) and at least as high as 70° C. (shipping and sterilization temperatures). Using a multilayer film allows the thickness of each layer to be adjusted to provide the desired physical characteristic. For instance, when forming a tray using the aforementioned M321 film, increasing the thickness of the polyethylene layer would provide a greater moisture barrier, while increasing the thickness of the polyester layer would provide greater stiffness. When a thicker film is used to form the container, that film must be sufficiently pliable for the floor of the container to form intimate thermal contact with the lyophilizer's shelf at least when the container is loaded with the product to be lyophilized.

The hydrophobic membrane used as roof 303 should allow water vapors crossing but inhibit bacteria from crossing. It should have a large fractional open area (product of pore area and number of pores divided by the total membrane area), either support itself or have a supportive backing, incorporate means to integrate it as roof 303 of bag 22. In addition, its product side should be compatible with the product being processed, and its external side should resist damage due to expected handling conditions. Tests have shown that thin PTFE membranes, being very inert and having relatively low resistance to vapor flow, are the membranes of choice (e.g. the aforementioned Emflon 0.2μ PTFE membrane). PTFE membranes, being flimsy and not heat sealable, preferably integrate a backing to support and protect the PTFE layer, as well as provide a sealant layer, said sealant adding little to the resistance of vapor flow. There are a few options in topping tray 308 with membrane 303 as the roof of chamber 305. The determining factors are whether membrane 303 integrates a sealant on the product side, external side or both, and the location of ports 314a and 314b. The descriptions given below should not be taken as limiting the scope of the invention, but as examples of preferred methods to seal membrane 303 to landing 308a.

FIGS. 3a and 3b illustrate one preferred method where membrane 303 has the external side (topside) of a PTFE layer laminated with a nonwoven layer (e.g. Typar® Spunbond polypropylene weighting 2 oz/yd², or 7 $mg/cm^2$, made by Snow Filtration West Chester Ohio) that supports and protects the PTFE against external damage and provides a sealant layer. Membrane 303 is sized such that its outside periphery 303a is larger than inside periphery 308b and smaller than outside periphery 308c of landing 308a. Frame 309, composed of at least a sealant material (e.g. aforementioned Typar®) and sized as landing 308a, and with its inside periphery 309a and outside periphery 309b preferably matching inside periphery 308b and outside periphery 308c of landing 308a respectively, is used to seal membrane 303 to landing 308a. To assemble, membrane 303 is laid on top of landing 308a, and frame 309 is laid on top of both membrane 303 and landing 308a. The three layers are then pressed with a heat sealer to seal the bottom of frame 309 to the exposed section of landing 308a as well as to the external (top) face of membrane 303 simultaneously. To maximize the functional area of membrane 303 over product 4, it is preferable that inside periphery 309a of frame 309, corresponds to inside periphery 308b of landing 308a. To further maximize effective membrane area, frame 309 preferably also consists of Typar® like water repellent yet breathable material that assures that if any product 4 is trapped in the stagnate area described below, it could also be lyophilized. Frame 309 preferably has a thickness between 0.002" and 0.020", said thickness depending on the degree of stiffness desired. Its width is nominally between ¼" to ⅝".

The combination of the area of membrane 303 over landing 308a that is not being sealed and the flexibility of landing 308a and membrane 303 may entrap product 4 in a stagnant area formed between said two layers. For example, when bag 22 is positioned upside down and lifted by its floor, it can cause landing 308a to move away from membrane 303 and allow product 4 to fill that space. This should be significantly limited and even eliminated when using supporting tray 528 with its rigid mating flange 529 as described in reference to FIGS. 5b and 5c. Otherwise, the stagnant area can be limited by stiffening membrane 303, at least its area over landing 308a, said stiffening achieved by using a frame 309 that is stiffer than that of landing 308a preventing the parting between membrane 303 and landing 308a. It is also possible to seal a second frame, like 309, to the underside of landing 308a stiffening the entire area of landing 308a further limiting landing 308a from flexing away from membrane 303 again limiting the aforementioned stagnation zone. By limiting the motion of landing 308a, frame 309 also adds stability to the rectangular shape of tray 308. It should also be understood that the material used for frame 309 should preferably correspond to a material that can be sealed (via heat, adhesive, or mechanical crimping) to tray 308.

Alternatively, a sealant layer (e.g. polypropylene) can be applied to the product side (underside) of membrane 303 along the area that membrane 303 overlaps landing 308a, so that membrane 303 can be sealed directly to landing 308a eliminating aforementioned stagnant zones and without adversely affecting vapor transfer rate. This design can be visualized by FIG. 3a less frame 309. Applying a sealant patterned along the outside periphery of membrane 303 is usually more expensive than laminating the entire surface. Thus, should the additional resistance to vapor flow due to a sealant layer is acceptable and the sealant is compatible with product 4, then a sealant layer can be applied to the entire product side of membrane 303 thereby eliminating frame 309 and reducing the width of landing 308a to that necessary to provide a functional seal between membrane 303 and tray 308. The external backing protects the membrane from damage during processing and use. Problems that may be introduced by product 4 seeing the product side of roof 303 that is less hydrophobic (i.e. the sealant rather than the PTFE membrane) can be reduced as described in reference to FIGS. 5a, 5b, 8a, 8b, 9a and 9b. If necessary landing 308a can be stiffened by sealing frame 309 to the topside of membrane 303 along landing 308a and/or second frame 311 to the underside portion of landing 308a, see FIG. 3c.

Figure 3C:
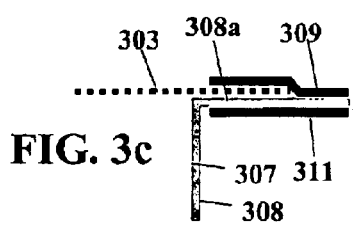
FIG. 3c is a cross sectional view of one preferred embodiment of the lyophilization bag incorporating a hydrophobic membrane and a bottom and a top-supporting frame.
Figure 3C:
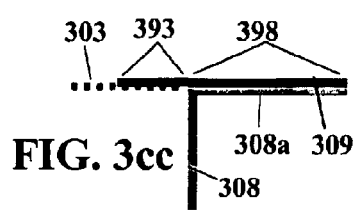

Another preferred design that eliminates the aforementioned stagnation between membrane 303 and landing 308a is shown in FIGS. 3a and 3cc. Here outside periphery 303a of membrane 303, which equals to but not larger than inside periphery 308b of landing 308a, is attached to landing 308a via frame 309. Frame 309, composed of at least a sealant material (e.g. aforementioned Typar®), has inside periphery 309a that is smaller than outside periphery 303a of membrane 303 such that when frame 309 is centered over membrane 303, they form overlap 393 shown in FIG. 3cc. Overlap 393 is used to seal frame 309 to the top surface of membrane 303. Similarly, outside periphery 309b of frame 309 preferably matches outside periphery 308c of landing 308a forming overlap 398 shown in FIG. 3cc that is used to seal frame 309 to landing 308a. Thus, by sealing frame 309 to both membrane 303 and tray 308, membrane 303 is incorporated as the roof of tray 308 eliminating the stagnation area seen when membrane 303 overlaps landing 308 as discussed in reference to FIG. 3c. To maximize the functional area of membrane 303 over product 4, it is preferable that outside periphery 303a of membrane 303 extends to inside periphery 308b of landing 308a and that the overlap between membrane 303 and frame 309 is minimized. An overlap between ¹⁄₁₆" and ⅛" should assure a reliable seal between membrane 303 and frame 309 without reducing the functional area by a meaningful amount (e.g. a 5" by 7" membrane area reduced by a ¹⁄₁₆" or ⅛" on each side would result in an area reduction of 2% and 4% respectively).

FIGS. 3ba and 3bb illustrate another innovative feature of membrane 303. Prior to lyophilization it can be shaped concavely relative to floor 302 of bag 22, see FIG. 3ba, distancing the membrane from product 4. Post lyophilization, during controlled rehydration, membrane 303 can be pushed in to form a convex shape profile, a shape that allows water 31 to be layered on its top to be contained, see FIG. 3bb. The water "puddle" has a vapor pressure controlled by its temperature. Thus, when gradual rehydration is desired, water placed on the membrane provides the water vapor to rehydrate product 4. Alternatively, bag 22 could be placed in a temperature controlled water bath to provide the water vapor to rehydrate the dried product in a simple and controlled manner. Once partially rehydrated, additional water may be added to complete the rehydration. In the field, bag 22 can be placed, membrane downward, in a water puddle thereby allowing the initial rehydration of the product while maintaining its sterility.

FIGS. 3a and 3b show ports 314a and 314b in fluid communication with product chamber 305, said ports used for introduction of product 4 into chamber 305 as well as reconstituting and administering lyophilized product 4. Such ports preferably incorporate standard adapters, as well known in the art, at their open ends such as a diaphragm (keeps sterility yet allow puncture with standard IV spike), latex or latex-like bulb for introduction of a liquid via a standard needle. To assure that product 4 easily and completely empties out of bag 22 at least the administration port is positioned at the bottom of chamber 305 when bag 22 is hung/suspended by eyelet 316. It is also important to limit, and preferably eliminate, any volume of product 4 in ports 314a and 314b prior to freezing. If necessary, additional ports can be added in a manner similar to that shown for ports 314a and 314b or other methods as described below. There are a few preferred means to incorporate ports 314a and 314b into bag 22, some preferred methods, without suggesting limitations to the scope of the invention, are given below.

Figure 3D:
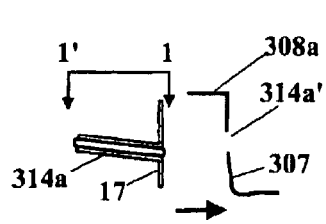
FIG. 3d is a cross sectional view of one preferred embodiment of the lyophilization bag having ports incorporated in its sidewall.
Figure 3E:
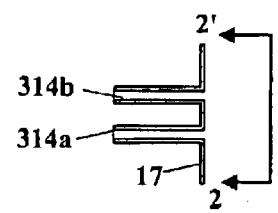
FIG. 3e is a cross sectional view of lyophilization bag shown in FIG. 3d viewed along line 1–1'.
Figure 3F:
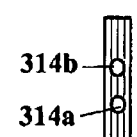
FIG. 3f is a cross sectional view of lyophilization bag shown in FIG. 3e viewed along line 2–2'.

FIGS. 3a, 3b, 3d, 3e, 3f and 4a to 4d illustrate typical methods to provide ports (e.g. ports 314a and 314b shown in FIG. 3e and ports 414a and 414b shown in FIG. 4a) with fluid communication with their respective product chambers. FIG. 3b illustrates ports 314a and 314b integrated into wall 307, said ports formed when tray 308 is vacuum formed. Alternatively, holes can be punched in wall 307 of tray 308 that correspond to the location of said ports and molded face plate 17 as shown in FIG. 3d, (and FIG. 3e viewed along line 1–1' of FIG. 3d and FIG. 3f viewed along line 2–2' of FIG. 3e), incorporating ports 314a and 314b to wall 307 such that the opening of ports 314a and 314b line up with corresponding holes 314a' (seen in FIG. 3d) and 314b' (not seen) in wall 307 as indicated by the arrow, assuring fluid communication with chamber 305.

Since any product left in ports 314a and 314b prior to freezing may not freeze or lyophilize as fast as the product in contact with the floor and in view of the membrane, it is best to avoid liquids accumulating in said ports. A variety of attachment methods as well known in the art (e.g. impulse heating, adhesives) can be used. Preferably, ports 314a and 314b are directed upward relative to floor 302 as measured by angle $\alpha$ in FIG. 3b, said upward direction assuring that any liquid of product 4 entering said ports would drip by gravity back down into chamber 305 when said floor is set horizontal against shelf 1. Angle $\alpha$ preferably is between 10° and 45°. Furthermore, to assure emptying of trapped liquid in said ports, the point of entry of said port into chamber 305 preferably should be placed above the expected liquid level of product 4.

In yet another design that limits product 4 residing in ports 314a and 314b, circular sections 314a' and 314b' of wall 307 aligned with ports 314a and 314b are thinned out but not punched through. Thinner circular sections 314a' and 314b' block product 4 from entering said ports as well as serve as a sterile diaphragm, much like those known in the art of IV bags. The user would place an IV spike into ports 314a and/or 314b, said spike being sharp enough and said circular section thin enough to have said spike piercing thin section 314a' and/or 314b' to form the desired fluid communications between product chamber 305 and said IV spike.

Figure 4A:
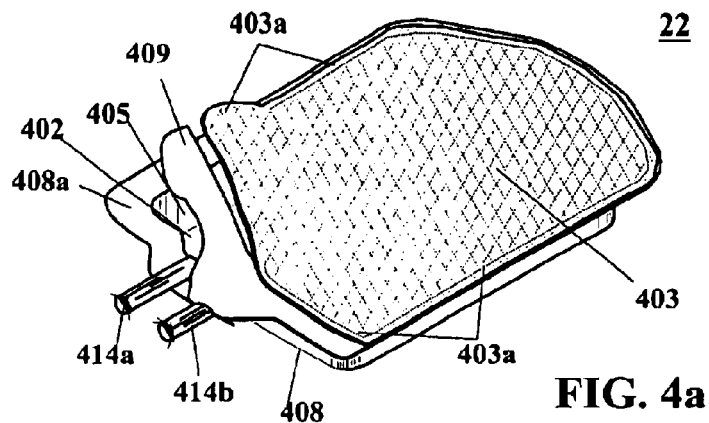
FIG. 4a is a three dimensional view of another preferred embodiment of the lyophilization bag having its ports sandwiched between the top of its product chamber and its roof.
Figure 4B:
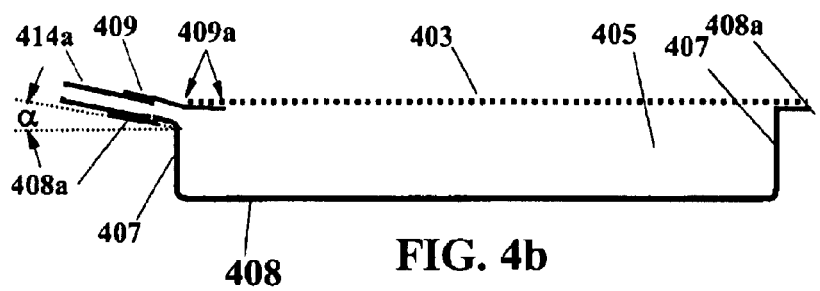

FIGS. 4a, a three dimensional view, and 4b, a cross sectional representation, illustrate another preferred design of tray 408 having wall 407, incorporating ports 414a and 414b into bag 22, by sealing them between landing 408a and frame 409 in a manner similar to that used for standard IV bags, to form a fluid communication with product chamber 405. To overcome the possible difficulty in sealing membrane 403 directly to landing 408a along the contours of ports 414a and 414b, a partial frame 409 is interposed between membrane 403 and said ports as shown in FIGS. 4a and 4b. Partial frame 409 is preferably sized to encompass ports 414a and 414b along landing 408a plus an additional width 409a that overlaps a small section of membrane 403 and is used to seal membrane 403 to partial frame 409, as indicated by arrows 409a in FIG. 4b. FIG. 4a is a three dimensional rendering of an empty bag 22 with partial frame 409 and its membrane 403 partially "peeled" away from landing 408a and ports 414a and 414b sealed between partial frame 409 and landing 408a. As shown, membrane 403 incorporates a sealant at least on its product side along its outside periphery 403a. Also, as described in reference to port 314a shown in FIG. 3b, ports 414a and 414b are directed upward relative to floor 402 as measured by angle $\alpha$, said upward direction assuring that any liquid of product 4 entering said ports would drip by gravity back down into chamber 405 when said floor is horizontal against shelf 1.

Figure 4C:
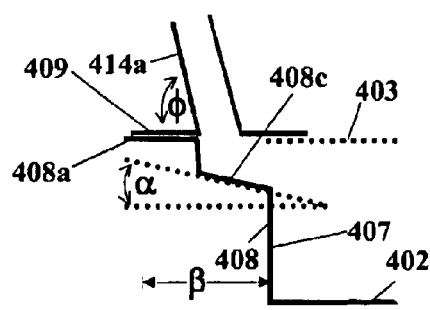
FIG. 4c is a cross sectional representation of a side view of a partial lyophilization bag shown in FIG. 4a but having its ports face upwards.

A modification of the design shown in FIG. 4a incorporating ports 414a and 414b in fluid communication with product chamber 405 is shown in FIG. 4c. Here ports 414a and 414b are incorporated into frame 409 much like they were to wall 307 as described in reference to FIGS. 3d–3f, except that said ports face upwards or preferably 60°±30° away from roof 403 as indicated by $\phi$ as a cross sectional representation in FIG. 4c. Tray 408 may be like 308 shown in FIG. 3b, or to minimize the area of the ports over the floor (i.e. maximize the unobstructed membrane area), tray 408 may have overhang section 408c that extends beyond floor 402 by $\beta$ seen in FIG. 4c. The value for $\beta$ equals the length required to incorporate ports 414a and 414b, typically between ⅜" and ⅝". Section 408c is preferably slanted up from the horizontal by $\alpha$, typically 10° to 45°, to assure that solution product entering that section would flow by gravity back to chamber 405 for the reasons described in reference to $\alpha$ in FIG. 4b. This design may simplify manufacturing and allow loading product 4 from the top of the container without reducing the membrane area available for lyophilization. Eliminating blocks in the membrane, e.g. as described in reference to the aforementioned prior art device, allows the membrane to be closer to the product without affecting sublimation rate. This feature reduces the required height of the container, increasing the ratio of product volume to product chamber volume, and thereby decreasing storage and processing costs.

Figure 4D:
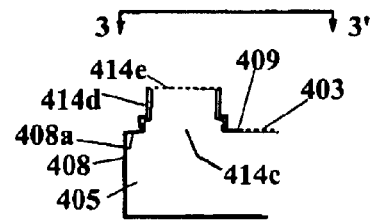
FIG. 4d is a cross sectional representation of one preferred embodiment of the lyophilization container having a large port, said port incorporating a hydrophobic membrane that facilitates lyophilization under said port.
Figure 4E:
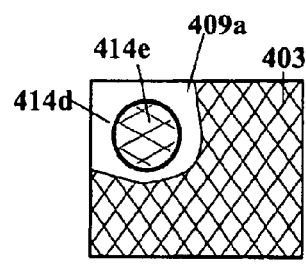
FIG. 4e is a cross sectional view of lyophilization container shown in FIG. 4d viewed along line 3–3'.

FIG. 4d illustrates a view of a partial cross section, and FIG. 4e is a partial cross section top view along line 3–3', of landing 408a incorporating large port 414c, having a first open area, in fluid communication with chamber 405 and topped with removable cap 414d used to close said port, said cap incorporating membrane 414e at its top. Membrane 414e reduces the blockage to vapor flow across roof 403 (inherent in the cap of aforementioned prior art containers) by the area said membrane corresponds to said first open area of said port 414c. It should be clear that cap 414d can be adapted to close port 414c in a variety of ways as well known in the art of caps used for bottles, such as with a screw-able or snap on mechanism. Preferably port 414c has an opening with an inside diameter between ⅜" and 1.0".

The desired flexibility of container 22 results in it deforming while being handled much like the shape of a filled IV bag changes due to gravity when taken off the table and hung up. To overcome this possible problem, a supporting tray that allows a flexible bag-like container to be handled and easily loaded onto the lyophilizer's shelf without introducing significant resistance to heat flow between the lyophilizer and the floor of the container 22 was designed. FIGS. 5a is a cross sectional view and 5b is a three dimensional view of supporting tray 528 and a flexible lyophilization container 22. Supporting tray 528 is made of a plate defined by outside perimeter 528e and a thickness "t" said plate having at least one cavity 525 defined by its depth "d" and its outside perimeter 525a. Perimeter 525a defines the size of lyophilization container 22 that supporting tray 528 can accommodate. Therefore, allowing for tolerance of manufacturing and ease of insertion perimeter 525a preferably should allow a clearance of ⅛" on each side of floor 302. Cavity 525 has floor 522 with an internal and an external side and vertical wall 527 surrounding floor 522. Surrounding cavity 525 is landing 528a that is defined by the difference between outside perimeter 528e of tray 528 and outside perimeter 525a of cavity 525. Tray 528 is used to support and facilitate handling of bag 22 as defined for example in reference to FIGS. 3a and 4a. Cavity 525 has depth of "d" which equals "H–y", where H equals the natural height between landing 308a and floor 302 (i.e. natural height of wall 307 of lyophilization container 22) and "y" equals the vertical distance that wall 307 is allowed to decrease to assure its floor 302 makes complete contact with the cavity side of floor 522. Preferably "y" should be less than 20% of H and more preferably less than 10% of H; a greater value for y/H may result in floor 302 expanding beyond their natural shape such that the product in that bottom portion of chamber 305, 4a in FIG. 5a, would see a folded wall 307 rather than the membranous roof 303. Supporting roof 303 above product 4 by tray 528 allows walls 307 of the Lyo-Bag 22 to be softer and more pliable, more like a standard IV bag made of PVC. Softer wall 307 makes it easier to collapse product chamber 305 for storage. It also expands the material that can be used to form tray 308 to films having Shore hardness of 80 A or less. The size of bag 22 to be used defines the depth of cavity 525. Floor 522 is typically between 1/16" and 5/8"; thicker floors are usually used for floors with larger footprint and/or more uniform temperature.

For applications where rapid cooling and uniform water content dictate a very thin thickness of product 4 (<1 mm), then pressure that the product exerts on the floor may be too low to achieve intimate contact between the floor and the shelf; a problem that must be resolved. FIGS. 5a and 5b illustrate means to enhance the thermal contact between floor 302 of bag 22 and floor 522 of supporting tray 528 in the form of channels 522a and 522b formed in floor 522. Channel 522a is in fluid communication with the lyophilizer and channels 522b form fluid communication between channel 522a and the bottom of floor 522. Thus, vacuum applied to the lyophilizer chamber is transmitted to the underside of floor 302 pulling it against floor 522. To achieve the best results with this system, it is best to apply some vacuum, preferably between −50 and −100 mmHg, prior to freezing product 4 when floor 302 is still pliable.

FIG. 5aa illustrates another mean to enhance the thermal contact between floor 302 of bag 22 and floor 522 of supporting tray 528 in the form of a thermal (e.g. aluminum) plate 32 adhered to the underside of floor 302 of bag 22. This plate can serve two purposes: it assures intimate thermal contact between floor 302 and itself, and it provides additional weight to enhance the thermal contact between its underside and shelf 1. Once lyophilization is completed this plate can be removed, and discarded if disposable, or reused.

FIG. 5b is a three-dimensional rendering of the proposed lyophilization system. It shows a multicavity tray 528 incorporating rigid mating flange 529, shown as a three-dimensional rendering in FIG. 5c, having outside perimeter 529e and opening 529f said opening having perimeter 529g that is preferably identical to outside perimeter 525a of cavity 525 of supporting tray 528. Mating flange 529 may also incorporate mating hole/slot 529c that accepts mating pins 528c of multicavity tray 528. Further, mating flange 529 may also incorporate rounded slots 529b that form a space for ports 314a and 314b of bag 22 when said bag is placed in multicavity tray 528 and then topped by mating flange 529. FIG. 5d is a three dimensional view illustrating how the end user would place lyophilization containers in supporting tray 528 shown in FIG. 5b. FIG. 5e is a three dimensional view illustrating supporting tray 528 shown in FIG. 5b filled with four lyophilization containers. FIG. 5f is a three dimensional view illustrating the alignment and placement of matching flange 529 to the top of filled supporting tray 528 shown in FIG. 5e. Landing 308a of bag 22 as shown in FIG. 5a would be sandwiched between landing 528a of supporting tray 528 and landing 529a of rigid mating flange 529 as shown in FIG. 5f. FIG. 5g is a three dimensional view illustrating filled supporting tray 528 shown in FIG. 5e topped with matching flange 529 shown in FIG. 5c ready to be placed in a lyophilizer. Placing bag 22 into cavity 525 so its landing 308a is supported by landing 528a, and then topping landing 308a with mating flange 529 so landing 308a is sandwiched in between, provides support for bag 22 and eliminates the need for second frame 311 used to stiffen landing 308a as described in reference to FIG. 3c. Typically mating flange 529 would be thinner than tray 528, its thickness dependent on the force required to hold landing 308a. Since tray 528 is preferably metal, and more preferably aluminum (light and with good thermal conductivity); it does not warp and does form an excellent thermal contact with shelf 1 of a lyophilizer. If greater thermal conductance is desired, then tray 528 can be made of copper or other high conductance material. Further, thermal conductance along floor 522 assures that a more uniform temperature is applied to floor 302 of bag 22 even if there are some contact discontinuities between the shelf side of floor 522 and shelf 1. Tray 528 and mating flange 529 preferably are made of anodized aluminum to enhance heat transfer between floor 522 of tray 528 and product 4. Further, walls 527 of cavity 525 provide additional heat transfer at least via radiation, and if contact is made between supporting tray's wall 527 and Lyo-Bag's wall 307, then by conduction as well. Any additional heat transfer should increase the lyophilization rate and may allow use of thicker layer of product 4 to be processed without sacrificing process time. For space saving sake, it is preferable that containers 22 have ports 314a and 314b facing inline with roof 303, and that landing 528a incorporates two circular indentions 528b to accommodate the circular shape of said ports. It is also preferred to add two pins 528c to tray 528 that line up with holes (or slots) 529c in mating flange 529, the combination of said pins and holes preventing flange 529 from sliding or falling off landing 528a and assuring opening 529f of flange 529 lines up over membrane 303 of container 22. Similarly, pins 528d can be added to accommodate hole 316 used to hang bag 22, said pins inserted into said holes to limit bag 22 from moving once placed in cavity 525. In addition, mating flange 529 may have corresponding holes 529d, which would accommodate for pins 528d.

For conditions where the heat transfer along wall 527 is irrelevant to the lyophilization process, then supporting tray 528 can be made by combining a thermoplastic structure shaped like matching flange 529 described above and a flat aluminum plate as floor 522. Thus, the thermoplastic structure provides wall 527, cavity 525 and landing 528a of tray 528 while the aluminum plate provides the heat transfer properties of floor 522. For bag 22 that incorporates aluminum plate 32 shown in FIG. 5aa, floor 522 would not be required. If floor 522 is made of a thin compliant tough plastic film such as polyurethane having a Shore hardness of 70 A and a thickness of 0.010" then it is possible to make the entire supporting tray from lightweight plastic. For this design to be functional, good contact must be made between the cavity side of floor 522 and the external side of floor 302, a requirement that dictates low coefficient of friction between said two floors, as for example having the surface of the polyurethane film matted.

Supporting tray 528 can also be made floorless. Though not shown, it can be described by visualizing an upside down mating flange 529. The floorless tray has an open bottom, allowing floor 302 of bag 22 to make direct contact with shelf 1. The height of wall 527 of supporting tray without floor 522 preferably is no higher than the height of wall 307. A higher supporting tray would limit the area that floor 302 makes contact with shelf 1.

Another major advantage for placing bag 22 within rigid tray 528 and topping it with matching flange 529 is that the stagnation area that may occur by membrane 303 lifting away from landing 308a, as described in reference to FIG. 3a, is eliminated. Thus, the weight of flange 529 pressing against landing 308a prevents membrane 303 from lifting away from landing 308a, a feature that allows greater freedom in the design of bag 22. It should be obvious that when using this system to eliminate product 4 from being trapped in said stagnation area, the best results are obtained by placing bag 22 in supporting tray 528 and topping it off with mating flange 529 prior to adding product 4 to product chamber 305. Limiting contact between membrane 303 and product 4 would assure cleaner unobstructed membrane and therefore a faster and more uniform lyophilization rate. Limiting contact between the membrane and the product increases in importance as the hydrophobicity of membrane 303 decreases (e.g. where sealant is on the product side of the membrane). By placing bag 22 in supporting tray 528 and fixing it with mating flange 529 prior to filling chamber 305 with product 4 renders flexible bag 22 with properties associated with a rigid tray. Further, by transporting bag 22 in a horizontal alignment, as maintained by supporting tray 528, limits the chance of product 4 contacting membrane 303. It should be clear that tray 528 need not have walls 527, but instead can have legs, as described in reference to FIGS. 8a and 8b, supporting its landing 528a above its floor 522, a design that would reduce the weight of tray 528. In addition, during the lyophilization process, having flange 529 pressing against landing 308a of bag 22 provides an additional force that maintains an intimate contact between floor 302 of bag 22 to shelf 1 of the lyophilizer throughout the lyophilization process.

The advantages of a system combining a rigid aluminum tray/mating flange system with lyophilization containers can be extended to handle containers used to lyophilize blood products or other products that are to be infused to a patient as well as products used in the pharmaceutical industry. Thus, lyophilization containers having a roof using membranes with pore's size greater than that required as a bacterial barrier can and should be used. Such containers can replace current open-faced containers widely used for lyophilization but with the added feature of conformable floor that enhances the lyophilization process and collapsible product chamber that significantly reduces storage space. To have a sterile product for the end user when membranes with pore size greater than $0.22\mu$ are used, either the lyophilizer is located in a clean room and/or the product is sterilized post lyophilization (e.g. gamma radiation).

Figures 7A, 7B, 7C:
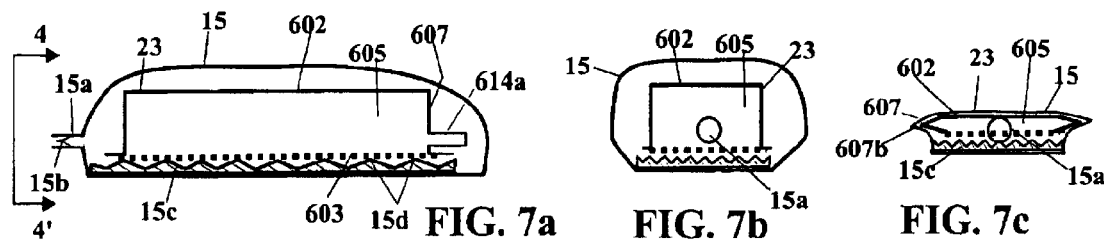
FIG. 7a is a cross sectional representation of one preferred embodiment of the lyophilization container in a protective over-pouch prior to said pouch being evacuated.
FIG. 7b is a cross sectional representation of FIG. 7a viewed along line 4–4'.
FIG. 7c is a cross sectional representation of FIG. 7b after said pouch has been evacuated.
Figure 8A:
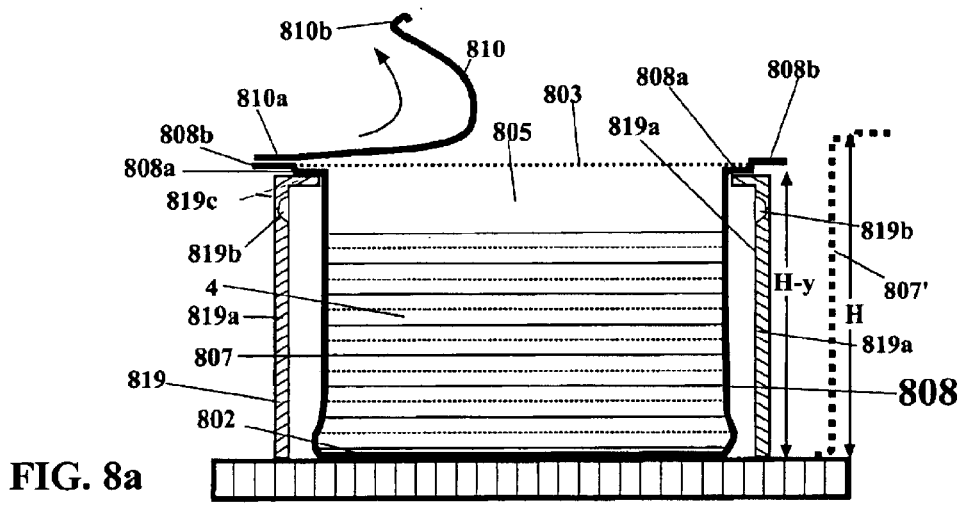
FIG. 8a is a cross sectional view of one preferred embodiment of the lyophilization container bag combined with a floorless disposable rigid supporting tray.

FIG. 8a illustrates another preferred embodiment consisting of disposable lyophilization container that utilizes the system previously described in reference to FIGS. 5a and 5b, said container consisting of tray 808 having floor 802, vertical walls 807, and roof 803 sealed to landing 808a that form product chamber 805. The underside of landing 808a is attached to and supported by disposable supporting frame 819, also shown in a three dimensional rendering in FIG. 8b. Supporting frame 819 consists of a top flange 819c and incorporates at least three legs 819a. Legs 819a have a length of H-y where H equals the height between landing 808a and floor 802 of product chamber 805 (i.e. natural height of wall 807 shown as a dashed line and labeled 807') and "y" equals the vertical distance that wall 807 is allowed to decrease to assure floor 802 makes complete contact with shelf 1. Preferably "y" should be less than 20% of H and more preferably less than 10% of H, a greater value for y/H may result in floor 802 expanding beyond their natural shape such that a portion of the product would see a folded wall rather than the membranous roof. Use of legs 819a to support roof 803 above product 4 allows walls 807 to be softer and more flexible much like a standard IV bag made of PVC. Legs 819a may also incorporate recess 819b that allows the user to break off said legs post-lyophilization and prior to over-pouching as described in reference to FIG. 7a. Though not shown, container product chamber 805 incorporates ports 814a and 814b in a manner similar to that described in reference to FIGS. 3a through 4d. Disposable frame 819 can be molded from rigid thermoplastics such as ABS, or PVC, or polypropylene.

Figure 8B:
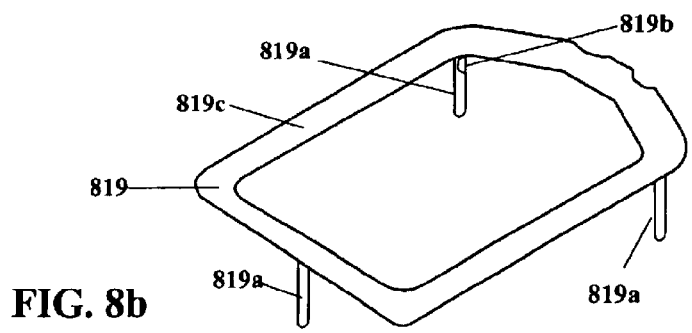

The design describing the floorless supporting frame shown in FIGS. 8a and 8b can be adopted to form a nondisposable supporting frame. Such a frame would not have the recesses used to break off its legs and it would rely on the weight of product 4 to keep floor 802 of product chamber 805 in intimate contact with the lyophilizer shelf as described in reference to floor 302 shown in FIGS. 3a and 3b. This floorless design of a supporting tray has the advantage that floor 802 is in direct contact with the lyophilizer shelf, a design that simplifies inserting the lyophilizer container into its support system by such means as allowing the user access to floor 802. It also assures that floor 802 does not "hang", as possible with walls 527 of supporting tray 528 described in reference to FIGS. 5a to 5g. Alternatively, the underside of floor 802 may incorporate thermal plate 32 as described in reference to FIG. 5aa.

As the pore size of hydrophobic membranes increases, its resistance to fluid flow decreases. Tests conducted by the inventor show that under the same lyophilization conditions (−30° C. and a vacuum of 20 mTorr), transport rates of water vapor across Pall Emflon PTFE membranes with the pore size of $0.2\mu$, $0.45\mu$, and $1.0\mu$ were 0.035, 0.048, and 0.068 gr/hr/cm$^2$ respectively. Use of membranes with larger pore size would therefore result in faster, less costly, lyophilization rate but it may be prohibited because the smaller size pores are required to maintain the barrier against bacteria. However, if the lyophilization process can be conducted in a clean environment, then, by keeping the membrane covered up to, and removing the cover just prior to, the lyophilization process allows the use of a larger pore membrane. To this end, Lyo-Bag 22 shown in FIG. 8a features peelable, preferably flexible, impermeable cover 810 designed to seal and protect membrane 803 during processing and handling prior to lyophilization. Just prior to lyophilization, cover 810 is removed. In general, cover 810 can be sealed along its periphery 810a to secondary landing 808b, said secondary preferably surrounding landing 808a. Cover 810 may also include tab 810b that extends beyond landing 808b to allow the user a handle to peel cover 810 off of landing 808b and expose membrane 803. As well known in the art of peelable adhesives, the adhesive used to seal cover 810 to landing 808b should withstand the processing yet allow the end user to peel cover 810 away from landing 808b without damaging membrane 803. Alternatively, a weakened section wall (e.g. thinner or perforated) between primary landing 808a and secondary landing 808b would allow the cover to be removed by tearing away secondary landing 808b from primary landing 808a and discarding said cover. If necessary, the same or a similar cover can be used to protect membrane 803 post-lyophilization.

Figures 6A, 6B:
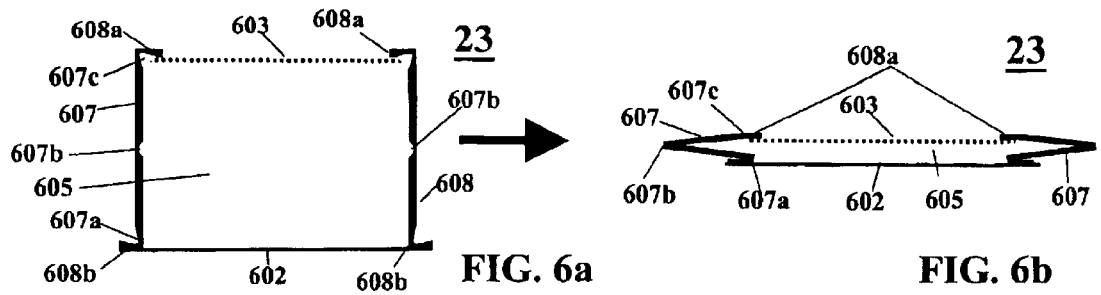
FIG. 6a is a cross sectional representation of one preferred embodiment of the lyophilization container having semi-rigid wall, said wall incorporating hinges that allow the end user to collapse its product chamber for more efficient storage.
FIG. 6b is a cross sectional representation of one preferred embodiment of the lyophilization container shown in FIG. 6a with its product chamber collapsed.

FIGS. 6a and 6b are a cross sectional representation of lyophilization container 23, another preferable embodiment of the present invention, composed of: an upside down semi rigid tray 608 similar in shape to tray 308 described in reference to FIGS. 3a and 3b whose bottom (now top) has been cut out to form top landing 608a extending inward, vertical wall 607, and bottom landing 608b extending outward. Conformable floor 602, possessing properties similar to floor 302 described in reference to FIG. 3b, is sealed along its outer periphery (e.g. impulse heating) to bottom landing 608b. Hydrophobic membrane, identical in character to previously described roof 303 in reference to FIG. 3a, is sealed along its outer periphery to top landing 608a to form roof 603 using manufacturing considerations described, for example, in reference to FIGS. 3a and 3b. As shown, the external side of membrane 603 is laminated with a sealant, breathable, and protective layer (e.g. aforementioned Typar®) and is sealed to the underside of landing 608a. The formed container is similar in shape and function to bag 22 having product chamber 605, conformable floor 602 and a hydrophobic membrane as roof 603 but its walls 607 being more rigid than flexible wall 307 as described in reference to FIG. 3a. The more rigid wall can be used in applications where product chamber 605 need not collapse as the reconstituted product is used. Tray 608 can be made from thermoformed biocompatible flexible material such as polypropylene, polyurethane, polyester, or polyethylene, preferably having a thickness between 0.003" and 0.030". Also the dimensions of bottom landing 608b and of top landing 608a preferably are only as wide as necessary to retain a reliable seal between floor 602 and roof 603 respectively, that being typically between ⅛" and ⅜".

Product chamber 605 having stiff wall 607 may still be minimized (e.g. for storage post-lyophilization) by incorporating 3 bendable hinges: bottom hinge 607a located between wall 607 and bottom landing 608b; top hinge 607c located between wall 607 and top landing 608a; and central hinge 607b located midway between said top and bottom hinges. All three hinges extend along the entire circumference of wall 607, thereby allowing hinged wall 607 to extend outward along hinge 607b and reduce the volume of product chamber 605 as well illustrated by FIG. 6a, showing the extended, and FIG. 6b showing the collapsed state of chamber 605. The hinges should render sufficient stiffness to assure that when container 23, filled with product 4, is topped with another product filled container 23 that the distance between floor 602 and roof 603 would decrease by no more than 10%. Thus, wall 607 must essentially remain stiff and support a weight equivalent to 2.0 gr/cm$^2$ (assuming a thickness of 2 cm of product 4, not shown in product chamber 605) plus the weight of tray 23 (nominally 0.1 gr/cm$^2$ of footprint). The minimum force required to bend all three hinges can be designed as a function of the maximum force they must withstand. Thus, for a container having floor 602 with an area $A_f$, and solution 4 to be processed having a maximum thickness of 2.0 cm, (yielding a force of 2.0 $A_f$ gr or a pressure of 1.5 mmHg), and requiring a safety factor of 10, suggests that the hinges should start bending with a force (gr) of 20 $A_f$. This force may be applied with a plate (not shown) pressing top landing 608a towards bottom landing 608b, or by applying a pressure difference across roof 603 (or floor 602) that is at least 15 mmHg higher outside chamber 605 than inside. The degree of collapse of chamber 605 is dependent on the reduction in distance between roof 603 and floor 602, a distance dependent on the location of central hinge 607b relative to the midpoint. It should be obvious that similar calculations can be made for other desirable products and/or product thickness used to load chamber 605. For example to be able to stack 5 lyophilization containers atop of each other, would require wall 607 of the bottom container to support a weight (with 10× safety factor) of 100 $A_f$ and a pressure difference of 75 mmHg. If it is desired to control the distance between roof 603 and floor 602 when chamber 605 is in the collapsed state, then central hinge 607b can be moved up away from midpoint and closer to top hinge 607c. This may be desirable when it is necessary to prevent "crushing" lyophilized product 4 during storage. It should be emphasized that this design allows floor 602 to be thinner and more conformable than wall 607. It also allows for a tray that is essentially rigid while processing and lyophilizing yet allow it to collapse to save on storage space that is so important post-lyophilization for the expensive refrigerated storage. It should be noted that the hinges can be designed such that wall 607 would preferably extend outward, as shown, or inward (not shown). The former would allow lower profile collapsed chamber 605 but with a larger footprint. The latter would allow a higher profile but with the footprint unchanged. Note that though not shown, container 23 incorporates ports much like, and in a manner similar to, that described for ports 314a and 314b in reference to FIGS. 3a through 4d. It should also be clear that a collapsed chamber 605 could be expanded again by either the user pushing central hinge 607b inward or by the introduction of the rehydrating solution.

Immediately post-lyophilization, lyophilization container 23 (or bag 22) preferably is placed within aluminized (e.g. Mylar film) over-pouch 15, much like those used in the blood collection industry (e.g. foil® pouch used for storing blood collection units model #4R3610, Baxter Travenol, Deerfield Ill.), said pouch acting as a barrier to transfer of $O_2$, $CO_2$, water and other gaseous molecules as well as light transmission and preserving now lyophilized product 4 as well as protecting container 23. Further pouch 15 is preferably evacuated (i.e. vacuum-sealed), a process that further limits the exposure of product 4 to trapped fluids in chamber 605 or within sealed space formed by sealed pouch 15 during storage, as well as reduce the volume of chamber 605 for more efficient storage. In one preferred embodiment, shown in FIG. 7a, lyophilization container 23 described in FIG. 6a is placed in and sealed within pouch 15. FIG. 7b shows a side view along line 4–4' of FIG. 7a. To facilitate the evacuation process, pouch 15 may incorporate port 15a along one of its walls such that once container 23 is sealed within pouch 15, vacuum can be applied to port 15a to evacuate the space within pouch 15 as well as the fluid contained in product chamber 605. As described below, the applied vacuum can also be used to collapse chamber 605. Port 15a may further incorporate one-way valve 15b, said valve allowing fluid flow out of, and not into, pouch 15. Alternatively or in addition to, port 15a may incorporate sealing means such that folding flexible port 15a and crimping said fold much like that done during blood processing. It should be obvious that pouch 15 preferably incorporates one of many means, known in the art of wrappers and pouches, that facilitate opening said sealed pouch to remove container 23 prior to use.

The expense of refrigerated storage space dictates that if lyophilized product 4 is to be refrigerated, it should be minimized in size. For example, a rectangular shaped package with a uniform thickness stores more efficiently than a circular package with a nonuniform thickness. Therefore, container 23 in evacuated pouch 15 preferably has a geometry with a rectangular footprint and a uniform thickness. Various methods can be incorporated to facilitate that geometry. For example, container 23 is placed in pouch 15 with its roof facing down; pouch 15 is sealed and mechanically compressed, as for example between 2 rigid plates (not shown), and then evacuated via port 15a. Preferably the combination compressing pouch 15, the stiffness of landing wall 607, and the degree of vacuum applied (greater vacuum would more likely buckle landing 308a) would suffice to assure that the external geometry of pouch 15 approaches the aforementioned ideal geometry. To prevent obstructing membrane 603 during the evacuation process and thereby facilitating the removal of gaseous molecules from product chamber 605, container 23 may incorporate means to provide an unhindered fluid path between said pouch and said membrane. For example, flat plate 15c described below and shown in FIGS. 7a–7c can incorporate protrusions 15d that prevent membrane 603 from being blocked during the evacuation process. It also prevents port 15a from being blocked by the collapsing walls of pouch 15. Once evacuated into the desired shape, it remains in that shape. For container 23 (or Lyo-Bag 22) that may buckle when pouch 15 is evacuated, flat rigid plate 15c, having a footprint larger than said container 23's or bag 22's footprint, is added to pouch 15. Now when bag 22 is placed in pouch 15, and pouch 15 is evacuated, flat rigid plate 15c assures that the evacuated package is flat and conforming to the shape of plate 15c as shown in FIG. 7c.

FIGS. 9a and 9b illustrate a system for lyophilization consisting of lyophilization container 24 and supporting tray 928. Preferably container 24 consists of pliable tray 908 having naturally flat rectangular shaped floor 902, said floor extending, along its outside periphery, to form vertical wall 907, said wall ending with landing 908a topped with a hydrophobic membrane serving as roof 903 to form product chamber 905. Preferably, the hydrophobic membrane is attached to the top of wall 907 along landing 908a. Ports 914a and 914b are incorporated into container 24 to form fluid communication with chamber 905. The preferred manufacturing means and choice of material used to form lyophilization containers 22 and 23 described for example in reference to FIGS. 3a–3f, 4a–4e, and 6a–6b can be used in forming container 24. Floor 902 of product chamber 905 should be sufficiently thin and pliable to assure it conforms to the surface it is placed on (i.e. floor 922 of supporting tray 928) when chamber 905 is filled with product 4, a requirement to assure the intimate contact between the two surfaces necessary for the most efficient thermal transfer between said two surfaces. Benefits of the rectangular shaped floor, intimate thermal contact, and the requirements to achieve said intimate contact previously described in reference to FIGS. 3a and 3b are just as applicable here for container 24 as they were there for container 22. It should be clear, as will be described below, that the circumferential support provided by wall 927 of cavity 925 to wall 907 of lyophilization container 24 maintains the shape of product chamber 905 even if a very pliable and thin film is used (e.g. a 0.005" thick polyurethane film having a Shore hardness of 65 A) to form tray 908. With such thin pliable film, tray 908 serves as a liner that takes the shape of cavity 925 that it is placed in. Hook 916 is placed opposite to ports 914a and 914b, and said ports can be used to line up and position container 24 in cavity 925 as well as extract the container. In addition, supporting tray has circular indentations 928b having an inside diameter equal to at least that of the outside diameter of ports 914a and 914b. The desired intimate contact that enhances lyophilization, can be further improved by incorporating channels in floor 922, much like channels 522a and 522b described in reference to FIGS. 5a and 5b.

Supporting tray 928 is designed to support and facilitate handling of lyophilization container 24. It is made of a plate defined by outside perimeter 928e and a thickness "t" said plate having at least one cavity 925 defined by its outside perimeter 925a and depth "d". Cavity 925 is further defined by its floor 922, having an internal and an external side, said floor surrounded by vertical wall 927. Surrounding the top of the cavity is landing 928a of flange 928 defined by the difference between outside perimeter 928e of tray 928 and perimeter 925a of cavity 925. The shape of cavity 925 preferably is identical to the bottom of container 24 but its size is slightly larger to accommodate manufacturing tolerances of the container as well as to facilitate inserting said container into said cavity. Thus, depth "d" of cavity 925, the height between landing 928a and floor 922, preferably is made to accommodate bag 24 such that its roof 903 is just below landing 928a. Depth "d" should preferably at least equal the expected maximum height of product 4 in chamber 905. Supporting bag 24 by tray 928 allows wall 907 to be softer and more pliable, more like a standard IV bag made of PVC. Softer wall 907 makes it easier to collapse product chamber 905 for storage. It also expands the material that can be used to form tray 908 to films having Shore hardness of 80 A or less. The size of bag 24 to be used defines the depth of cavity 925. Floor 922 is typically between $\frac{1}{16}$" and $\frac{5}{8}$"; thicker floors are usually used for floors with larger footprint and/or more uniform temperature. For example, to lyophilize 100 ml of a platelet solution with a preferred thickness of 5 mm, floor 902 of bag 24 would have an area of 200 cm$^2$ (e.g. 16.0 cm long×12.5 cm wide), and the height of wall 907 would be greater than 5 mm, preferably above 10 mm and less than 15 mm. The higher value can be used when there is greater chance of membrane 903 contacting product 4 due to membrane 903 sagging, wall 907 not being sufficiently stiff, or due to splashing when tray 928 is handled after containers 24 have been filled. Less vigorous handling and better membrane support allow use of wall 907 with a lower height. Thus, the opening of cavity 925 defined by perimeter 925a should be at least 16.0 cm×12.5 cm but preferably 16.5 cm×13.0 cm. The latter larger opening allows easier insertion and lining up of bag 24 into cavity 925. To limit air being trapped in cavity 925 by wall 907 of bag 24 seating against wall 927, and to further facilitate insertion of bag 24 into cavity 925, holes 927g and 928g are drilled into wall 927 to form fluid communication with cavity 925. The lower profile containers can be used by providing additional support to membrane 903 such as described in reference to membrane 303 in FIGS. 3a, 3b, 3c, 5a and 5b.

Another simple feature appropriate to the system shown in FIGS. 9a to 9d is illustrated in FIGS. 9c and 9d by supporting rod 930. Supporting rod preferably extends across the midsection along the length of membrane 903, said rod further affixed along its bottom length corresponding to the top of membrane 903 by such methods as adhesives or heat sealing. The latter is especially useful if said rod is polypropylene and the top of membrane 903 is laminated with a polypropylene layer as described previously in reference to FIG. 3a. It should be obvious that each bag 24 can incorporate a rod 930, and for a very long bag multiple rods can be used. Rod 930 should not interfere with the collapse product chamber 905 and needs to extend beyond the width of bag 24 just sufficiently to support weight of membrane 903. As a relative size, for the aforementioned 16.0 cm long×12.5 cm wide bag, rod 930 is preferably a 14 cm long polypropylene rod with an effective diameter of $\frac{1}{8}$".

FIG. 9c illustrates the steps taken to load containers 24 into supporting tray 928 and FIG. 9d illustrates a fully loaded supporting tray. It should be clear that supporting trays can be made with a greater number of cavities to handle greater number of units of container 24, said number of cavities can be simply calculated from the size of the lyophilizer's shelf divided by the area of floor 902 of container 24 and the minimum additional area required for landing 928a. It should be obvious to the reader that the design considerations described for supporting tray 528 and bag 22 in reference to FIGS. 5a and 5b apply here as well. In fact, it should be further clear that designs, material, structure, and processes described for one embodiment should be taken as applicable to other embodiments where appropriate.

An example combining some of the concepts of the invention follows. Four Lyo-Bags 22 are each placed in a cavity of supporting tray 528 and the supporting holes over the corresponding pins shown in FIG. 5f. The supporting holes of rigid frame 529 are lined up with supporting pins of supporting tray and then pushed down against landing 308a of each bag. If necessary it is possible to tighten flange 529 against landing 308a and to landing 528a to prevent landing 308a of bag 22 from moving. Once flange 529 is in place, product 4 is introduced to chamber 305 of each bag and the 4-cavity tray is placed in the lyophilizer and the process is commenced. The aluminum tray is removed from the lyophilizer, the bags removed from tray and placed in a storage over-pouch, the over-pouch is sealed and evacuated via port 15a shown in FIGS. 7a, 7b and 7c and the package placed in storage. When the product is to be used, the over-pouch is removed, bag 22 placed membrane up, and the product rehydrated in a control manner, reconstituted completely and then administered.

Figure 10A:
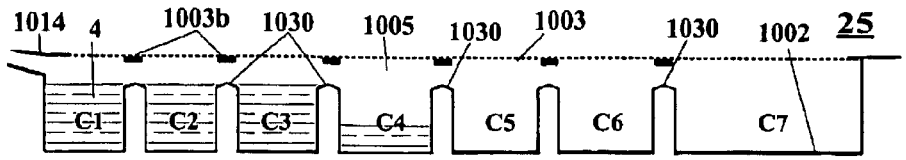
FIG. 10a is a side view of one preferred lyophilization container having multicavity with a common port.
Figure 10B:
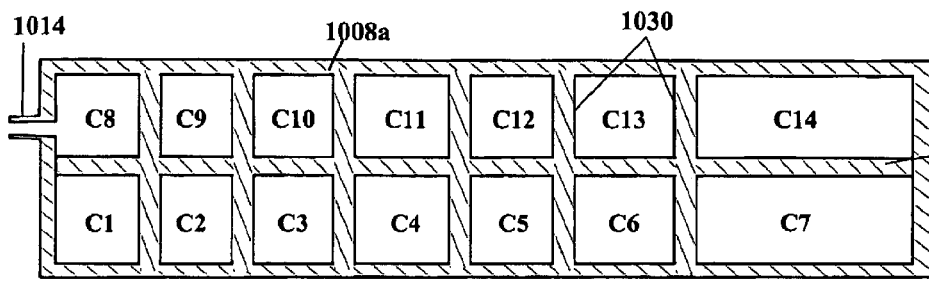
Figure 10C:
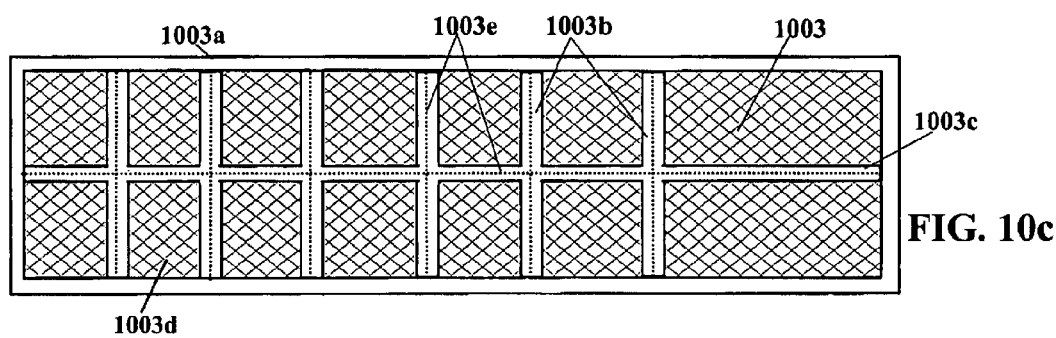

In applications where it is desired to produce a multidose product from a single large unit then a multicavity container 25 illustrated in FIGS. 10a–10f can be used. FIG. 10a is a side view of container 25 prior to being filled. FIG. 10a is a side view and FIG. 10b is a top view of container 25. As shown, a compatible film, such as the previously mentioned 0.007" thick medical film M321 made by Cryovac, or other laminates such as the combination of ECDEL or PETG for strength with EBAC for flexibility and sealability (Eastman Chemical, Longview Tex. 75608), is vacuum formed into a tray with 14 cavities (e.g. C1 to C14 shown in FIG. 10b). The cavities are separated by weirs 1030 and their volume can be of equivalent C2 v. C9 in FIG. 10b) or different (e.g. C6 v. C7 shown in FIG. 10b). As shown in FIG. 10b, the cavities can be formed as identical parallel sets divided by common septum 1008b. Common roof 1003 incorporating a hydrophobic membrane, (a bottom view of the roof is shown in FIG. 10c) is sealed along outside periphery 1008a of the vacuum formed tray, but not to the top of weirs 1030, to form common chamber 1005. Product 4 to be dried is introduced into common chamber 1005 via common port 1014. As illustrated in FIG. 10a, if container 25 is positioned with its floor horizontal then cavity C1, the closest to port 1014 fills first, followed by cavity C2, C3 and so on. The weirs assure that a cavity is completely filled prior to the others cavities being filled.

Figure 10D:
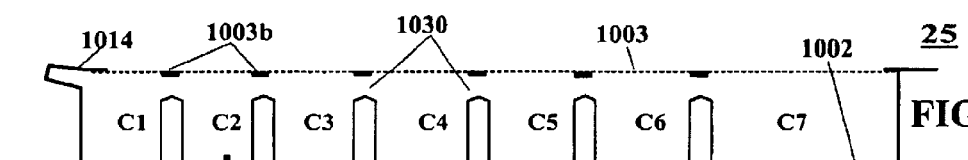
FIG. 10d is a side view of the container shown in FIG. 10a prepared to be fitted in its supporting tray.
Figure 10E:
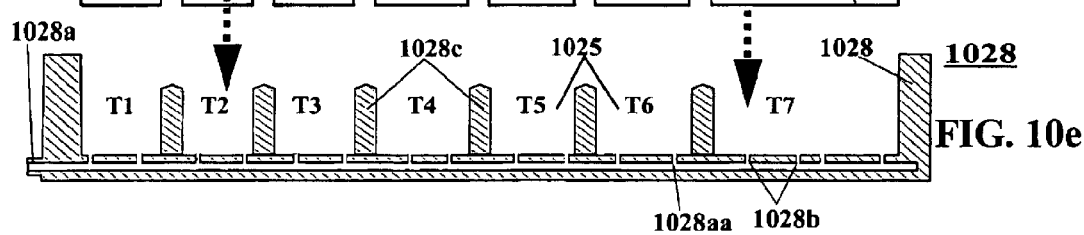
Figure 10F:
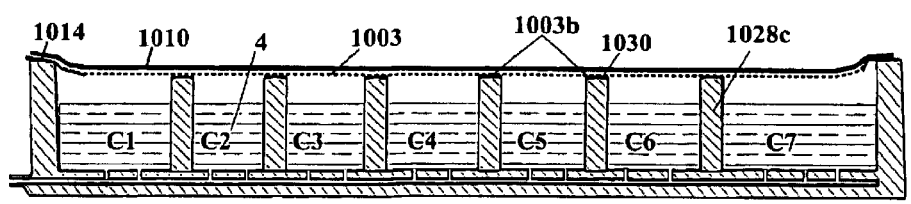

FIGS. 10d to 10f show container 25 mating with supporting tray 1028. As shown, posts 1028c are inserted into the underside of weirs 1030 with the underside of floor 1002 of each cavity making intimate contact with floor of supporting tray 1028. As discussed with reference to FIGS. 5a and 5b, this intimate contact can be enhanced by applying vacuum to channels 1028aa and 1028b made in the base of supporting try 1028. The vacuum, applied to port 1028a, forces the floor of container 25 against supporting tray 1028. Channels 1028aa and 1028b also assure that during lyophilization, any air left between the floors of container 25 and supporting tray 1028 can escape to the lyophilizer chamber rather than expand and lift the floor of the container away from the floor of the supporting tray. Supporting tray 1028 preferably is made of aluminum or copper, acts as a thermal plate that provides uniform temperature across its contact with the floor of container 25.

Roof 1003 incorporates means to seal the product side of the roof to the top of the weirs thereby isolating each of the cavities to form individual pockets with product 4. For this purpose, the underside of roof 1003 incorporates sealing means 1003b and 1003c that adhere to the top of weirs 1030 and the common septum 1008b respectively. Posts 1028c of supporting tray 1028 provide a structure against which outside of membrane 1003 can be forced to mate with the top of the individual weirs 1030. Sealing means 1003b shown in FIGS. 10a, 10c and 10d located on the underside of roof 1003 are formed in a pattern that matches weirs 1030 shown in FIG. 10b. For example, the seal can be made by using a pressure sensitive adhesive. Alternately, a thermosealant (e.g. EBAC) applied to the underside of the membrane can be sealed to the top of the weirs by using a heated plate that squeezes the top of roof 1003 against the weirs supported by posts 1028c. While sealing the roof to the weirs, port 1014 of container 25 can be sealed as well. The final container divided into individual pockets is shown in FIG. 10f. Though the seal between membrane 1003 and the top of the individual weirs 1030 can be made prior to lyophilization, it is preferable to seal it post lyophilization. With the latter, roof 1003 can be sealed simultaneously while sealing the container within an impermeable cover 1010 as shown in FIG. 10f. Cover 1010 serves a similar function to that of film 810 described in reference to FIG. 8a and pouching material 15 described in reference to FIG. 7a. Cover 1010, which protects the dried product from rehydration, is shaped like roof 1003 shown in FIG. 10c and is sealed along the pattern described by sealant 1003a, 1003b and 1003c of roof 1003 shown in FIG. 10c. It is also preferable to incorporate tear-seal lines 1003e, shown by the dotted line in FIG. 10c, along the seals separating the 14 pockets. The tear-seal lines allow the user to tear open one pocket at a time without affecting the integrity of the product sealed in the other pockets. Though not shown, it should be clear that if the film used to form container 25 is insufficient to maintain dried product 4 dry, then it too can be covered with impermeable film 1010.

Figure 11A:
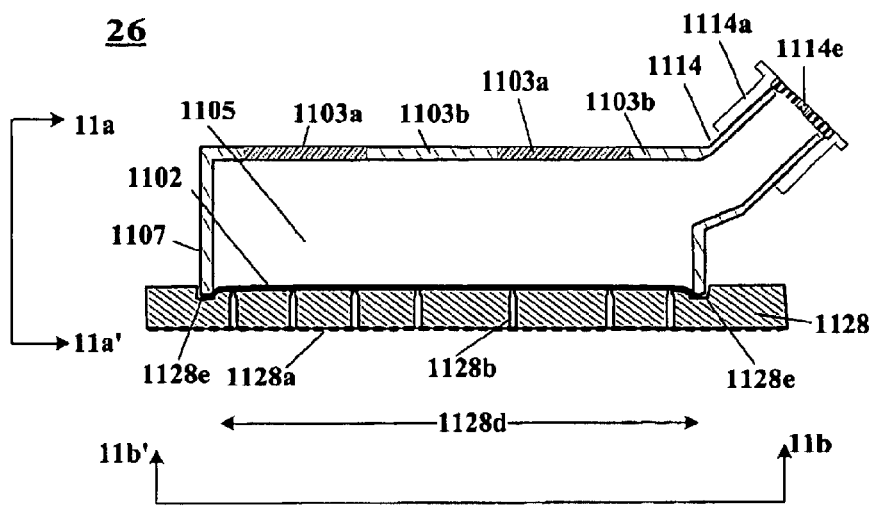
FIG. 11a is a side view of one preferred lyophilization container, the Lyo-Flask placed atop its thermal plate.

When drying products having low volume but a large surface area (e.g. cells adhering to the floor of a culture dish), the force exerted by the weight of product may be insufficient to displace a compliant floor to form intimate contact with the shelf of a lyophilizer. Further, containers used to process (grow) adhering cells should be transparent to allow the user to examine the growing cells. These requirements dictate that means to assure intimate contact between the floor of the container and the shelf of the lyophilizer and that the roof of the container incorporate a transparent section to allow viewing the cells is incorporated. FIG. 11a is a side view of a tissue culture flask 26 (e.g. Falcon #353802) modified to meet the aforementioned requirements. As shown, flask 26 is preferably made of polystyrene for clarity and rigidity with a portion of its roof composed of a hydrophobic membrane 1103a that allows water vapor but not liquids to cross while maintaining sterility of the product. The other portion of roof 1103b is sufficiently clear to see the product in chamber 1105 or on floor 1102. In one form of the invention, floor 1102 of the flask is made of a thin biocompatible film preferably having a thickness between 0.001" to 0.015" that is bonded to the bottom of vertical walls 1107 of flask 26. The film's physical properties are such (thin and flexible) that it can conform atop specially designed thermal plate 1128. As described in reference to channels 1028aa and 1028b shown in FIG. 10e, channels 1128a and 1128b are incorporated in thermal plate 1128 to allow air trapped between the underside of floor 1102 and the top side of plate 1128. Channels 1128b are holes drilled through the thickness of plate 1128, see FIG. 11a.

Figure 11B:
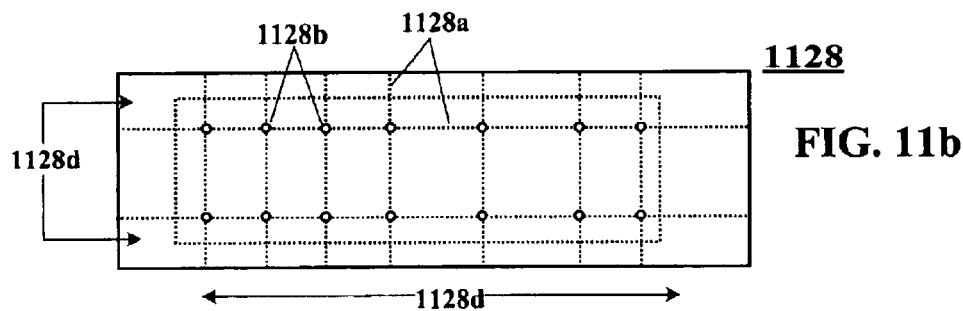

FIG. 11b is a bottom view taken along 11b and 11b' of the thermal plate shown in FIG. 11a. Channels 1128a as shown in FIG. 11b, are fine grooves cut along the length and width of the underside of plate 1128 crossing holes 1128b thereby forming fluid communication between the top side of plate 1128 and the lyophilizer even when plate 1128 is placed on shelf 1, see FIG. 11c. As with standard flasks, flask 26 has a neck like shape port 1114 covered with screw-on-cap 1114a. Cap 1114a can incorporate a hydrophobic membrane 1114e.

To further assure that floor 1102 forms intimate contact with thermal plate 1128, floor 1102 is stretched over the top surface of plate 1128. This is achieved by having the top surface of plate 1128 slightly convex (e.g. its center is between 0.001" and 0.020" thicker than its periphery). Further, the top surface of plate 1128 also incorporates groove 1128e shown in FIGS. 11a and 11c. Groove 1128e has an inside periphery that matches the periphery of floor 1102. The width of groove 1128e is slightly wider than the thickness of vertical wall 1107 of flask 26 so as to assure that the wall and the edge of floor 1102 fit in the groove as shown in FIGS. 11a and 11c.

Figure 11C:
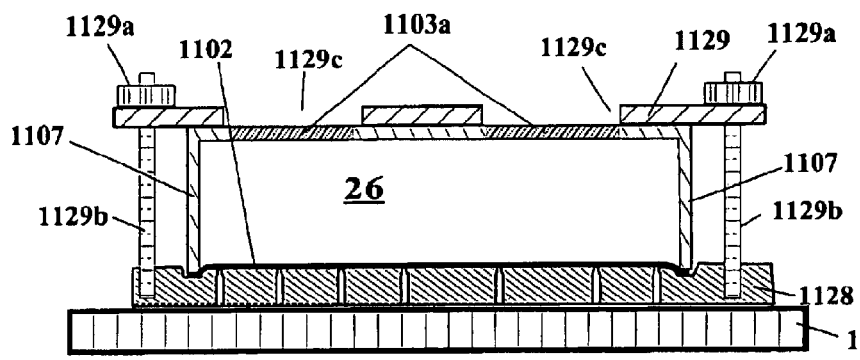
FIG. 11c is a side view taken along 11a and 11a' of the container and thermal plate shown in FIG. 11a and an illustration of one preferred means to enhance the intimate contact between the floor of the container and the thermal plate.
Figure 11D:
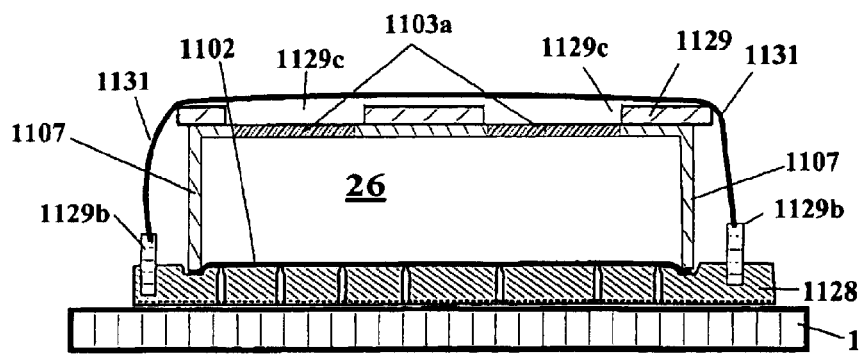
FIG. 11d is a side view taken along 11a and 11a' of the container and thermal plate shown in FIG. 11a and illustrating elastic means to enhance the intimate contact between the floor of the container and the thermal plate.

FIG. 11c is a side view of flask 26 taken along line 11a–11a' of flask 26 shown in FIG. 11a, as well as an illustration of one preferred means to enhance the intimate contact between thermal plate 1128 and floor 1102 is achieved. As shown, studs 1129b, secured by thread to thermal plate 1128, extend above the height of flask 26. Top plate 1129 has holes to allow it to be placed over the studs and additional holes 1129c to ensure that membrane 1103a in the roof of flask 26 is free to breath. The user would position the floor of flask 26 within groove 1128e then place top plate 1129 over studs 1129b, push the plate against the top of flask 26, and then tighten nuts 1129a to force walls 1107 into groove 1128e thereby stretching floor 1102 against convex section 1128d to form the desired intimate thermal contact between floor 1102 and thermal plate 1128. Since the underside of plate 1128 is flat, it will make good thermal contact with the shelf 1 of the lyophilizer. Other means, such as weights (e.g. using a thicker and heavier top plate 1129) or elastic bands 1131 (see 1131 FIG. 11d), can be used to force floor 1102 against thermal plate 1128.

It should be clear that the product side of floor 1102 should be compatible with the application in use. Thus, for cell culture, where cells need to adhere to floor 1102, the surface of floor 1102 can be charged using vacuum gas plasma, or coated with collagen, fibronectin, or other cell friendly "coats" that promote cell adhesion and growth.

It should also be clear that post drying of the product, the hydrophobic membrane incorporated in the roof of Lyo-Flask 27, 28 and 29 must be sealed with an impermeable film much like that described for cover 1010 in reference to FIG. 10f and cover film 810 in reference to FIG. 8.

Another preferred embodiment of flask 26 is to have its floor 1102 made of the same material as its walls, a design that mimics a standard tissue culture flask (e.g. Falcon #353802) with only its roof modified as describes in reference to membrane 1103a in FIG. 11a. A standard flask has "feet" in the form of a ridge along the outside periphery of its bottom. These "feet" help prevent scratching of the underside of the floor and aid in stacking one flask atop another. Preventing the floor from contacting surface to prevent scratching also prevents good thermal contact with the floor of a lyophilizer. This problem is solved by shaping the top surface of thermal plate 1128 to accept the geometry (e.g. feet along the outside periphery, and slight curvature) of the underside of floor 1102. It should be noted that though polystyrene is considered rigid, it does flex at the thickness used for culture flasks (approx. 0.020 inches). This flexibility, together with the known geometry, allows forming a thermal plate with a matching top surface. The matching surfaces and the means to enhance intimate contact between thermal plate 1128 and floor 1102 shown in FIG. 11a provide improved heat transfer.

It should also be clear that the designs described in FIGS. 11a to 11c for a single culture flask are easily applied to multiwell flasks (e.g. Falcon #353224). Further, the design for multicavity tray described in reference to FIGS. 10a to 10f can be combined with the design described in reference to FIGS. 11a to 11c. Thus for example, the present invention also reads on a rigid multiwell flask with its floors made of a thin compliant film and the roof of each well incorporating a hydrophobic membrane. Further, each well can be sealed with its roof as shown in FIG. 10f, thereby separating the wells to allow for individualized pockets of product, with each pocket accessible without affecting the other pockets.

Another preferred embodiment of the present invention is Lyo-Dish 27, a modified culture dish (e.g. Falcon #353801). One form of which is shown as a side view in FIG. 12a and as a top view in FIG. 12b. Lyo-Dish 27 is composed of a circular dish having vertical wall 9 1207, floor 1202 and roof 1203 forming sealed chamber 1205. Chamber 1205 sealed to liquids but not gases. Liquids can be introduced or withdrawn via side port 1214. Port 1214 can, for example be a female Luer fitting. Walls 1207 and floor 1202 are made of polystyrene as the standard culture dishes are. Roof 1203 incorporates hydrophobic membrane 1203a that allows transport of water vapor but not liquids while maintaining sterility. Roof 1203 also has a clear section 1203b that allows viewing of cells growing on floor 1202. The area of membrane 1203a should be as large as possible while leaving sufficient clear area on the roof to allow viewing of growing cells 1204. The membrane can for example; cover anywhere from 10% to 90% of the product side area of the roof, but preferably the membrane area is between 25% and 75% of the roof area. Hydrophobic membrane 1203a can be one large membrane, as shown in see FIG. 12b, or for better distribution, a few smaller membranes as shown in FIGS. 13 and 14. Roof 1203 also incorporates wings 1203c, shown in FIGS. 12a, 12b, 16a and 16b. These wings have an inside perimeter that is slightly larger than the outside perimeter of floor 1202 and therefore, as shown in FIG. 16b, provide means to stack one Lyo-Dish atop another. Here is an example of the Lyo-Dish in use. Cells introduced via port 1214, settle and adhere along floor 1202. If desired, the Lyo-Dish can be placed in an incubator to promote cell growth. To remove and replenish the cell culture medium, a syringe can be placed in Luer fitting 1214, the dish turned upside down with port 1214 facing downward and the liquid withdrawn. As the liquid is withdrawn, membrane 1203a allows air to enter chamber 1205 thereby preventing any generation of suction in chamber 1205. Fresh culture medium can be added in a similar manner except that it is preferred that port 1214 faces upwards. Once cells have grown to the desired density, they are exposed to stabilizing agents (e.g. Trehalose) and then either lyophilized or desiccated. Once dried, the Lyo-Dish is pouched in a manner similar to that described in reference to FIG. 7a. Rehydrating the product can be achieved in a manner similar to that described in reference to FIG. 3bb.

FIG. 15 illustrates a side view of another Lyo-Dish, 28, which is identical to that described in the FIG. 12a except that its port 1514a extends to the bottom of chamber 1505. Lyo-Dish 28 is composed of a circular dish having vertical walls 1507, floor 1502 and roof 1503 forming sealed chamber 1505. Chamber 1505 is sealed to liquids but not gases. Product is introduced or withdrawn via top port 1514a that extends via tube 1514 to the bottom 1514b of chamber 1505. The extension of port 1514a allows exchanging liquids without turning Lyo-Dish 28 upside down, as is required for Lyo-Dish 27. Port 1514a can, for example be a female Luer fitting. Walls 1507 and floor 1502 are made of polystyrene as found in standard culture dishes. Roof 1503 incorporates hydrophobic membrane 1503a that allows transport of water vapor but not liquids while maintaining sterility. Roof 1503 also has a clear section 1503b that allows viewing of cells growing on floor 1502.

FIG. 16 illustrates a side view of another Lyo-Dish, 29, which is also similar to Lyo-Dish 27 described in FIG. 12a. Lyo-Dish 29 is composed of a circular dish having vertical walls 1607, floor 1602 and roof 1603, forming sealed chamber 1605. Chamber 1605 is sealed to liquids but not gases. Floor 1602 is formed of a compliant thin walled film similar to film 1108 described in reference to FIGS. 11a and 11c. Product or culture medium is introduced or withdrawn via port 1614. Port 1614 can be Luer fitting or a latex free septum that allows the use of needles to introduce/withdraw liquids from chamber 1605. Port 1614 is recessed below the top surface of roof 1603. This recess allows a top port Lyo-Dish to be stacked upon each other as shown in FIG. 16b. Wall 1607 is made of polystyrene as the standard culture dishes are. Roof 1603 incorporates hydrophobic membrane 1603a that allows transport of water vapor but not liquids while maintaining sterility. Roof 1603 also has a clear section 1603b that allows viewing of cells growing on floor 1602. Pliable floor 1602 allows the use of thermal plate 1628, having channels 1628a and 1168b which serves the same purpose as thermal plate 1128 having channels 1128a and 1128b described in reference to FIGS. 11a, 11b and 11c.

It should be obvious that by utilizing means to enhance the thermal intimacy between the floors of Lyo-Dishes 27, 28 and 29 and the floor of the lyophilizer, that heat exchange and thereby lyophilization rates can optimized. Thus, the combination of top plate 1129, posts 1129b and nuts 1129a as described in reference to FIG. 11c and elastic means shown in FIG. 11d with Lyo-Flask 26 can also be used for the Lyo-Dishes.

It should be obvious that the size of the port used for the various containers described above can vary to accommodate their respective applications.

While the usefulness of the innovative container has been described mostly in terms of freeze-drying, it is applicable for other methods of drying biological products. For example drying by desiccation would also benefit from features of the container such as its tray-like shape, roof that allows vapor to cross but not bacteria, efficient heat transfer, collapsibility for storage, and simple means for controlled rehydration.

It should be understood that a comprehensive description of each of the applications of the invention is beyond the scope of a patent application and therefore the aforementioned descriptions are given as illustrations and should not be used to limit the intent, spirit, or scope of the invention.

With that in mind, I claim:

1. A container for drying a biological product to be placed on a shelf of a drying chamber, said container comprising
   a) a tray having a product side compatible with said product, said tray defining;
      i) a floor having a first inside periphery, an inside surface contacting said product, and an underside surface contacting said shelf;
      ii) a vertical wall extending upward along said first inside periphery, said wall having a second upper periphery, said vertical wall and said floor forming at least two wells;
   b) a roof having a first area, said roof incorporating a hydrophobic membrane having a second area, said membrane providing vapor communication with said drying chamber while retaining said product within at least two said wells, said at least two wells and roof joined to form at least two sealed pockets for containing said product;
   wherein each of said pockets may be filled with said biological product, and wherein once the product is dried, said product in one pocket can be separated, rehydrated, and used without affecting the product in other pockets.

2. A container for drying biological products as claimed in claim 1 wherein said container further incorporates first means for providing efficient thermal transfer between said floor of the container and said shelf of a drying chamber.

3. A container for drying biological products as claimed in claim 2 wherein said first mean for providing efficient thermal transfer between underside of said floor of the container and said shelf, said mean is a thermally conductive plate having a first footprint, said thermal plate interposed between the underside of the floor of the container and the shelf, said thermal plate having a top that conforms to the shape of the underside of the floor of the container, and a bottom side that forms an intimate thermal contact with the shelf.

4. A container for drying biological products as claimed in claim 3 wherein the drying chamber is a lyophilizer and wherein said thermal plate further incorporates second means that assure intimate thermal contact under conditions of lyophilization between the thermal plate and the underside of the floor of the container.

5. A container for lyophilizing biological products as claimed in claim 4 wherein said second means that assure intimate thermal contact between the top of the thermal plate and the underside of the floor of the container under conditions of the lyophilization process are channels incorporated along the surface of the thermal plate, said channels providing a first fluid communication between the top of the thermal plate and the underside of the floor of the container, said fluid communication providing a passage way for air entrapped between the top of the thermal plate and the underside of the floor of the container to escape to the lyophilization chamber.

6. A container for lyophilizing biological products as claimed in claim 5 wherein said second means that assure intimate thermal contact between the top of the thermal plate and the underside of the floor of the container under all the conditions of the lyophilization process wherein the thermal plate further incorporates at least one hole forming a second fluid combination between the top side of the thermal plate and the channels along the bottom surface of the thermal plate, said combination of channels and at least one hole providing a passage way for air, trapped between the top of the thermal plate and the underside of the floor of the container, to escape.

7. A container for drying biological products as claimed in claim 4 wherein further the floor of the container is pliable and said second means that assure intimate thermal contact between the top of the thermal plate and the underside of the floor of the container under conditions of the lyophilization process is allowing the pliable floor of the container to be stretched over the top surface of the thermal plate.

8. A container for drying biological products as claimed in claim 7 wherein said stretching of the pliable floor of the container is improved by further having the top surface of the thermal plate convex.

9. A container for drying biological products as claimed in claim 8 wherein said top surface of the thermal plate is having a center with a first thickness and a third periphery having a second thickness, said first thickness being thicker than second thickness, said difference between the thicknesses defining the convex shape of the top surface of the thermal plate.

10. A container for drying biological products as claimed in claim 3 wherein the thermal plate is made of copper.

11. A container for drying biological products as claimed in claim 3 wherein further the vertical wall is rigid and the second means assuring intimate thermal contact between the top of the thermal plate and the underside of the floor of the container further include a top plate, said top plate having:
 a) a second footprint;
 b) means to position the top plate over the thermal plate;
 c) a first set of holes that ensure that the hydrophobic membrane incorporated in the roof of the container is free to breath when the top plate is placed over the roof of the container;
 d) a third means that presses the top plate against the roof of the container thereby pushing the floor of the container against the top of the thermal plate to enhance the intimate thermal contact between the floor of the container and the top of the thermal plate.

12. A container for drying biological products as claimed in claim 11 wherein the second foot print of the top plate is equal to the first footprint of the thermal plate.

13. A container for drying biological products as claimed in claim 11 wherein the second footprint of the top plate is smaller than the first footprint of the thermal plate.

14. A container for drying biological products as claimed in claim 11 wherein the floor of the container is pliable.

15. A container for drying biological products as claimed in claim 11 wherein the top surface of the thermal plate further incorporates at least one groove that accepts the underside of the floor of the container.

16. A container for drying biological products as claimed in claim 11 wherein the third means that presses the top plate against the roof of the container are the combination of threaded studs secured to and extending from the thermal plate, and matching nuts, said nuts when tightened, pushing the top plate against the rigid wall of the container thereby pushing the container against the thermal plate to form intimate thermal contact between the floor of the container and the top of the thermal plate.

17. A container for drying biological products as claimed in claim 11 wherein the third means that presses the top plate against the roof of the container is the weight of the top plate, said weight pushing the container against the thermal plate thereby forming an intimate thermal contact between the floor of the container and the top of the thermal plate.

18. A container for drying biological products as claimed in claim 11 wherein the third means that presses the top plate against the roof of the container is at least one elastic band, said elastic band pushing the container against the thermal plate thereby forming an intimate thermal contact between the floor of the container and the top of the thermal plate.

19. A container for drying biological products as claimed in claim 3 wherein the first footprint of the thermal plate has a third outside perimeter, said outside perimeter being larger than the first inside periphery of the floor of the container.

20. A container for drying biological products as claimed in claim 1 wherein said vertical wall is rigid.

21. A container for drying biological products as claimed in claim 1 wherein said floor of the container is a thin biocompatible film having a thickness between 0.001" to 0.015".

22. A container for drying biological products as claimed in claim 1 wherein the container is further used to store the product and provides a means to rehydrate the product in a controlled manner prior to the use of the product.

23. A container for drying biological products as claimed in claim 22 wherein said means to rehydrate the product in a controlled manner is water vapor transfer across the hydrophobic membrane.

24. A container for drying biological products as claimed in claim 1 wherein said container further incorporates at least one port in fluid communication with at least one of said wells, said port used to introduce said biological product into at least one of said wells.

25. A container for drying biological products as claimed in claim 24 wherein further said port incorporates a screw-on-cap to cover said port.

26. A container for drying biological products as claimed in claim 1 wherein the roof first area is larger than the second area of the hydrophobic membrane, and wherein further, a third area of the roof, defined as the first area less the second area, is sufficiently clear to see the product in the container.

27. A container for drying biological products as claimed in claim 26 wherein the second area of the membrane is between 25% and 75% of the first area of the roof.

28. A container for drying biological products as claimed in claim 26 wherein the second area of the membrane is formed by more than one membrane.

29. A container for drying biological products as claimed in claim 1 wherein the biological product is a product contains cells to be dried.

30. A container for drying biological products as claimed in claim 29 wherein the cells to be dried are stem cells.

31. A container for drying biological products as claimed in claim 1 wherein further includes a barrier that seal and protects said membrane post drying, as well as protect the product from being exposed to water vapor and light.

32. A container for drying biological products as claimed in claim 31 wherein said barrier is a pouch.

33. A container for drying biological products as claimed in claim 32 wherein at least the floor of the container is made of a material that promote cell adhesion and growth.

34. A container for drying biological products as claimed in claim 33 wherein at least the floor of the container is made of polystyrene.

35. A container for drying biological products as claimed in claim 1 wherein the container is further used to grow cells.

36. A container for drying biological products as claimed in claim 1 wherein said container incorporates at least two pockets for drying one or more biological products, wherein each of said pockets may be separately filled with said one or more biological products, and wherein once dried, the product in one pocket can be separated, rehydrated, and used without affecting the product in the other pocket.

37. A container for drying biological products as claimed in claim 36 wherein said container incorporates multiple pockets containing the biological product with each of said pockets having a geometry that allows dispensing of the product in the individual pockets.

38. A container for drying biological products as claimed in claim 37 wherein further the roof is covered with an impermeable cover, said cover protecting the dried product from rehydration, said cover sealed to the roof along said second upper periphery and said cover incorporating tear-seal lines that allow the user to tear open one pocket at a time without affecting the integrity of the product sealed in the other pockets.

39. A container for drying biological products as claimed in claim 37 wherein the multiple pockets of said container is formed as multiwell flasks.

40. A container for drying biological products as claimed in claim 36 wherein the roof of each pocket incorporates a hydrophobic membrane.

41. A container for drying biological products as claimed in claim 36 wherein the pockets are formed from a common chamber to form two or more wells separated by weirs, said weirs forming at least a portion of said second upper periphery of said vertical wall.

42. A container for drying biological products as claimed in claim 41 wherein the roof of the container incorporates means to seal the product side of the roof to the top of the second upper periphery thereby isolating each of the wells to form individual pockets.

43. A container for drying biological products as claimed in claim 42 wherein said means to seal the product side of the roof to the top of the second upper periphery of the wells is adhesion.

44. A container for drying biological products as claimed in claim 42 wherein said means to seal the product side of the roof to the top of the second upper periphery utilizes a supporting tray that provides a structure against which the roof can be forced to mate with the second upper periphery of the individual wells.

45. A container for drying biological products as claimed in claim 42 wherein said means to seal the product side of the roof to the top of the second upper periphery is heat.

46. A container for drying biological products as claimed in claim 45 wherein further the product side of the roof incorporates a thermo-sealant thereby facilitating said heat sealing means.

47. A container for drying biological products as claimed in claim 42 wherein further said container incorporates a port, said port configured to be sealed simultaneously when sealing the product side of the roof to the top of the second upper periphery.

48. A container for drying biological products as claimed in claim 42 wherein further includes an impermeable pouch so that the container may be sealed within said impermeable pouch, said pouch protecting the dried product from rehydration, said pouch sealed simultaneously when the product side of the roof is sealed to the top of the second upper periphery of the vertical wall.

49. A container for drying biological products as claimed in claim 36 wherein the pockets accommodate a specific volume of biological product and wherein the specific volume accommodated by the first pocket is different from the specific volume of the other pockets.

50. A container for drying biological products as claimed in claim 1 wherein said container can be further used to collect, process, dry, store, and reconstitute the biological product.

51. A container for drying biological products as claimed in claim 50 wherein said container further maintains the biological product sterile.

52. A container for drying biological products as claimed in claim 1 wherein said product is red blood cells.

53. A container for drying biological products as claimed in claim 1 wherein said product is mesenchymal cells.

54. A container for drying biological products as claimed in claim 1 wherein said wells are formed as cell culture dishes having at least one rigid wall.

55. A container for drying biological products as claimed in claim 1 wherein said floor and said wall are made of the same material.

56. A multiwell flask system for drying a biological products to be placed on a shelf of a drying chamber, said multiwell flask comprising:
   a) a tray having a product side compatible with said product, said tray defining;
      (i) a floor having a first inside periphery, an inside surface contacting said product, and an underside surface contacting said shelf;
      (ii) a multiplicity of vertical walls extending upward along said first inside periphery, said walls having a second upper periphery, said vertical walls and said floor forming at least two wells;
   b) a roof having a first area, said roof incorporating a hydrophobic membrane having a second area, said membrane providing vapor communication with said drying chamber while retaining one or more products within said at least two wells, said at least two wells and roof joined to form at least two sealed pockets for containing said one or more products;
   c) at least one port in fluid communication with each well, said port used to introduce said biological product into said wells.

57. A multiwell flask system for drying biological products as claimed in claim 56 wherein said system further includes a thermal plate, said plate having a topside, said top side having multi-cavities, the number of said cavities corresponding to the number of wells of the flask system, said cavities shaped to accept the underside surface of the multiwell flask thereby enhancing thermal contact between said underside of said flask and thermal plate.

58. A culture dish for drying a biological product to be placed on a shelf of a drying chamber, said culture dish comprising:
   a) a floor having a first inside periphery, an inside surface contacting said product, and an underside surface contacting said shelf;
   b) a vertical wall extending upward along said first inside periphery, said wall having a second upper periphery, said vertical wall and said floor forming at least two wells;
   c) a roof having a first area, said roof incorporating a hydrophobic membrane having a second area, said membrane providing vapor communication with said drying chamber while retaining said product within said wells, said at least two wells and said roof joined to form at least one sealed pocket for containing said product;
   d) at least one port in fluid communication with at least one well, said port used to introduce said biological product into at least one said well;
   wherein the first area of the roof is larger than the second area of the hydrophobic membrane, and wherein further, a third area of the roof, defined as the first area less the second area, is sufficiently clear to see the product in at least one of the wells.

59. A container for drying biological products as claimed in claim 58 wherein further the second area of the membrane is composed of at least two membranes incorporated in the first area of the roof.

60. A multiwell flask for drying a biological product to be placed on a shelf of a drying chamber, said multiwell flask comprising:
- a) a tray having a product side compatible with said product, said tray defining;
    - (i) a floor having a first inside periphery, an inside surface contacting said product, and an underside surface contacting said shelf;
    - (ii) a vertical wall extending upward along said first inside periphery, said walls having a second upper periphery,
    - (iii) one or more weirs extending from the floor and joining vertical wall to form at least two wells;
- b) a roof having a first area, said roof incorporating a hydrophobic membrane having a second area, said membrane providing vapor communication with said drying chamber while retaining one or more products within said at least two wells, said at least two wells and roof joined to form at least two sealed pockets for containing said one or more products;
- c) at least one port in fluid communication with each well, said ports used to introduce said biological product into said wells.

61. A multiwell flask for drying a biological product as claimed in claim 60 wherein a said flask contains a single port, said port used to fill all the wells.

62. A multiwell flask for drying a biological product as claimed in claim 60 wherein said flask is formed of pliable material.

63. A multiwell flask for drying a biological product claimed in claim 60 wherein said second area of said membrane equals the first area of said roof.

64. A multiwell flask for drying a biological product as claimed in claim 60 wherein once said product is dried, the product in one pocket can be separated, rehydrated, and used without affecting the product in the other pockets.

65. A multiwell flask for drying a biological product as claimed in claim 60 which further utilizes a thermal plate designed to enhance hear transfer between the shelf of a drying chamber and a product to be dried, said plate having a topside and a bottom side, said topside of said thermal plate making intimate thermal contact with the outer side of the container and said bottom of said thermal plate making intimate thermal contact with the shelf of the drying chamber.

66. A multiwell flask for drying a biological product as claimed in claim 65 which further utilizes wherein further the thermal plate is used to support and handle the multiwell flask with product to be dried.

67. A multiwell flask for drying a biological product as claimed in claim 65 wherein the thermal plate further improves the uniformity of the heat transfer across said floor.

68. A container for drying a biological products in a drying chamber having a shelf to place said container, said container comprising
- a) a tray having a solution side compatible with said product, said tray defining;
    - i) a floor having a first inside periphery, an inside surface contacting said product, and an underside surface contacting said shelf; said floor formed of a pliable material that easily conforms to said shelf;
    - ii) a vertical wall extending upward along said first inside periphery, said wall having a second upper periphery, and a landing extending from said second upper periphery, said vertical wall and said floor forming at least two wells;
- b) a roof, said roof incorporating a hydrophobic membrane, said membrane providing vapor communication with said drying chamber while retaining said product within at least two said wells, said floor, vertical walls and roof joined to form at least two sealed pockets for containing said product;
- c) at least one port in fluid communication with said pocket said port used to introduce into said pocket and or remove from said pocket said product;
- d) said floor sufficiently pliable that said floor conforms, by the weight of said product in the container, to the surface of said shelf thereby assuring the intimate contact between the two surfaces necessary for the most efficient thermal transfer between said shelf and said solution via said floor.

\* \* \* \* \*